(12) United States Patent
Soo et al.

(10) Patent No.: US 9,089,677 B2
(45) Date of Patent: Jul. 28, 2015

(54) TRANSCUTANEOUS MULTIMODAL DELIVERY SYSTEM (TMDS)

(75) Inventors: B. Chia Soo, Beverly Hills, CA (US); Kang Ting, Beverly Hills, CA (US); Ben Wu, San Marino, CA (US); Kevin Zhang, West Covina, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/358,391

(22) Filed: Jan. 25, 2012

(65) Prior Publication Data

US 2012/0220981 A1 Aug. 30, 2012

Related U.S. Application Data

(60) Provisional application No. 61/436,128, filed on Jan. 25, 2011.

(51) Int. Cl.
*A61M 37/00* (2006.01)
*A61M 9/00* (2006.01)
*A61K 9/00* (2006.01)

(52) U.S. Cl.
CPC .......... *A61M 37/0015* (2013.01); *A61K 9/0021* (2013.01); *A61M 2037/0023* (2013.01); *A61M 2037/0046* (2013.01); *A61M 2037/0053* (2013.01); *A61M 2037/0061* (2013.01); *Y10T 29/49826* (2015.01)

(58) Field of Classification Search
CPC ........... A61K 9/0021; A61M 37/0015; A61M 2037/0023; A61M 2037/0046; A61M 2037/0061; A61M 2037/0053
USPC .......... 604/57–64, 309, 103, 46, 173
See application file for complete search history.

(56) References Cited

U.S. PATENT DOCUMENTS

| | | | |
|---|---|---|---|
| 8,109,904 B1 * | 2/2012 | Papp | 604/103.01 |
| 8,858,912 B2 * | 10/2014 | Boyden et al. | 424/9.1 |
| 2002/0082543 A1 * | 6/2002 | Park et al. | 604/21 |
| 2007/0260201 A1 * | 11/2007 | Prausnitz et al. | 604/272 |
| 2008/0183144 A1 * | 7/2008 | Trautman et al. | 604/272 |
| 2008/0213461 A1 | 9/2008 | Gill et al. | |
| 2008/0269685 A1 * | 10/2008 | Singh et al. | 604/173 |
| 2009/0035446 A1 * | 2/2009 | Kwon | 427/2.1 |
| 2009/0182306 A1 | 7/2009 | Lee et al. | |
| 2012/0219589 A1 * | 8/2012 | Garcia De Castro Andrews et al. | 424/227.1 |

OTHER PUBLICATIONS

International Search Report for PCT/US2012/022605 mailed Aug. 27, 2012, 7 pgs.

* cited by examiner

*Primary Examiner* — Theodore Stigell
*Assistant Examiner* — Benjamin Koo
(74) *Attorney, Agent, or Firm* — DLA Piper LLP (US)

(57) ABSTRACT

A transcutaneous multimodal delivery device for drug delivery and the methods of making and using the same are provided.

39 Claims, 7 Drawing Sheets

TRANSCUTANEOUS MULTIMODAL DELIVERY SYSTEM (TMDS)

CROSS-REFERENCE TO RELATED APPLICATION

This application claims the benefit of U.S. provisional patent application No. 61/436,128 filed on Jan. 25, 2011, the teaching of which is incorporated hereto in its entirety by reference.

BACKGROUND OF THE INVENTION

1. Field of the Invention

This invention is directed to therapeutic medical devices and methods of making and using the same.

2. Description of the State of the Art

Burns are one of the most common and devastating forms of trauma (reviewed in Church et al.)[5]. Data from the U.S. National Center for Injury Prevention and Control show that approximately 2 million fires are reported each year which result in 1.2 million people with burn injuries[5]. Moderate to severe burn injuries requiring hospitalization account for approximately 100,000 of these cases, and about 5,000 patients die each year from burn related complications[5]. Annual burn care costs in the United States exceeds US$18 billion dollars[5].

When significantly injured, the skin's ability to fight infection, maintain fluid balance, and regulate temperature is compromised until skin integrity is restored[6]. A major burn is defined as >25-30% total body surface area (TBSA) partial burn ($2^{nd}$ degree) and full-thickness burn ($3^{rd}$ degree) or >10% full-thickness burn[7]. Burns are further broken down into 3 distinctive zones: coagulation, stasis, and hyperemia[8]. The zone of coagulation/necrosis forms the nonviable burn eschar nearest to the heat source[8]. The zone of stasis surrounds the central necrosis area and comprises tissue that is initially viable but, due to hypoperfusion and ischemia, may die and join the zone of coagulation/necrosis. Thus, burn wound necrosis can increase over time (termed burn wound progression or conversion) as release of inflammatory mediators and tissue edema (from the original burn injury as well as from resuscitation of the burn injury), or infection further compromises blood flow to already critically injured/ischemic tissues[9]. The zone of hyperemia, which surrounds the zone of stasis, comprises non-injured tissue with increased blood flow as a compensatory reaction to the burn[8].

Burn wound infection control is critical because bacteria release various inflammatory substances such as endotoxins and oxygen free radicals that can increase burn wound conversion[10]. The zones of coagulation and stasis are the greatest sources of infection entry. Current infection control for burns involves maintenance of a moist healing environment, application of topical antimicrobials until spontaneous healing (for partial thickness burns), and/or early excision and wound coverage with split thickness skin grafts (STSG)(for full thickness or deep partial thickness burns)[11,12]. Burn wound conversion create a "moving target" situation in which the TBSA of necrotic tissue requiring excision and grafting can progressively increase in the first few days after thermal trauma[13,14]. On top of this, once the extent of burn requiring excision and closure is demarcated, the definitive treatment, autograft skin, is limited in supply—which further prolongs time to complete definitive wound closure. Thus, strategies to minimize burn wound progression/conversion (i.e., minimize tissue excision) and enhance wound closure success rates (i.e., maximize skin graft "take") can accelerate recovery and decrease the morbidity and mortality of burn patients.

Disruption of the normal skin barrier in major burns alters immune function, producing an imbalance between pro- and anti-inflammatory cytokine syntheses and increasing susceptibility to post burn infection and sepsis[8,15]. Necrotic tissue and protein-rich wound exudates in burned tissue provide a rich growth medium promoting rapid bacterial colonization—even with modern topical antimicrobial use[16,17]. And due to poor blood flow to necrosis and stasis burn zones, systemic antibiotics do not decrease burn wound cellulitis or sepsis[18,19].

Historically, burn wound infection has been the most common cause of mortality in thermally injured patients[11]. However, even with more modernized care of early wound excision/closure and topical antimicrobials, approximately 75% of all deaths in patients with severe burns over 40% TBSA are related to sepsis from burn wound infection or other infectious complications and/or inhalation injury[18]. Thus, while the overall incidence of burn wound infections has declined with implementation of early wound excision/closure; the data are inconclusive for large burns[10,11]. This underscores the need for better infection control in large burns.

The types of bacteria that colonize and infect burn patients and their antimicrobial susceptibilities are influenced by both the patient's body flora and the hospital environment flora[20]. But as a general guideline, resident gram-positive skin flora such as *Streptococcus pyrogenes* and *Staphylococcus aureus* (*S. aureus*) that reside within skin appendages initially colonize the wound in the first 24-48 hours[11]. By 48-72 hours, endogenous gram-negative organisms from respiratory or gastrointestinal sources such as *Pseudomonas aeruginosa* (*P. aeruginosa*), *Klebsiella pneumoniae*, and *Escherichia coli* (*E. coli*) begin populating the burn eschar and may predominate by day/In addition, US military personnel injured in Iraq or Afghanistan as well as burn patients in the US have found increased infection by multidrug-resistant *Acinetobacter calcoaceticus-baumannii*[11]. Meanwhile, delayed fungal infections (average 16 days from time of injury) (e.g., *Candida* species or *Aspergillus* species) can also occur and is regarded as an independent predictor of mortality[21]. From Table 1, *S. aureus* and coagulase negative *Staphlococcus* appear to be the most common gram-positive organism isolated, while

TABLE 1

Common Organisms Identified in Burn Wounds

| Top 5 Organisms -% Prevalence | Specimen Method | Study Time Frame/ Sample Collection Time Frame | Country/ # Patients | Average % TBSA (Range) | Topical Therapy Used | Reference |
|---|---|---|---|---|---|---|
| Coag neg *Staph* −44.3 *S. Aureus* −30.4 | Swabs from | May to November | Turkey 80 | 22.9 (5-75%) | Silver sulphadiazine | Erol et al.[17] |

TABLE 1-continued

Common Organisms Identified in Burn Wounds

| Top 5 Organisms –% Prevalence | Specimen Method | Study Time Frame/ Sample Collection Time Frame | Country/ # Patients | Average % TBSA (Range) | Topical Therapy Used | Reference |
|---|---|---|---|---|---|---|
| P. aeruginosa –12.5 Enterobacter spp. –2.6 Candida spp. –1.9 | wound, nares, axilla, groin, umbilicus | 2002 Swab within 12 hrs of injury, 7 d, 14 d, 21 d | | | | |
| Pseudomonas spp. –36 S. aureus –19 Klebsiella spp. –16 Proteus spp. –11 E. faecalis –9 | Swabs from wounds | * June 1993 to June 1997 Patient collection time frame not specified | India # patients not specified | N.S.[A] | N.S. | Revathi et al.[22] |
| MRSA[B] –40.7(I)[C] 45.6(II) Acinetobacter –10.2(I) 15.5(II) MRSE[D] –14.4(I) 2.9(II) Pseudomonas –12.7(I) 2.9(II) Mixed –12.7(I) 15.6(II) | N.S. | June 1992 to May 1996 (Group I) June 1996 to May 2000 (Group II) | Kuwait 943 (Group I) 939 (Group II) | 46% (10-90%; I) 40% (2-95%; II) | Silver sulphadiazine | Bang et al.[18] |
| S. Aureus 29(Bx)[E] 35(S) Coag neg Staph 23(Bx) 21(S) P. aeruginosa 17(Bx) 20(S) Acinetobacter 10(Bx) 11(S) Enterobacter 9(Bx) 12(S) | 3 mm punch or scalpel AND alginate swab | "2 year period" No other information provided | UK 74 | N.S. | N.S. | Steer et al.[23] |

[A]N.S.—not specified
[B]MRSA—methicillin resistant S. aureus
[C]I indicates Group I and "II" indicates Group II patients
[D]MRSE—methicillin-resistant S. epidermidis, a subgroup under coagulase-negative Staphylococcus
[E]"Bx" indicates biopsy; "S" indicates swab Pseudomonas and Acinetobacter are the most common gram-negative organisms. Thus, desirable infection control would require broad spectrum coverage against gram positive and negative organisms and ideally, fungi.

Presumptive diagnosis of an invasive bacterial infection is made when biopsied burn tissue contains >$10^5$ bacteria/gram tissue; however, the most reliable way to establish true tissue invasion is histological evidence of bacteria in viable tissue adjacent to or underneath the eschar (reviewed in[5,12]). With respect to the speed and morbidity associated with bacterial infection, Barret et al. performed quantitative bacteria cultures in 20 consecutive pediatric patients averaging 34±5 TBSA burns. Twelve of 20 patients had burn excision/closure within 24 hours of injury, while 8/20 had delayed excision/closure (7 d±2d). All patients were treated with silver sulfadiazine before surgery. Quantitative cultures revealed $10^4$ bacteria/gram tissue in the burn eschar and $10^2$ bacteria/gram tissue in the remaining post-excision wound bed for the acute excision group. In contrast, the delayed excision group exhibited up to $10^6$ bacteria/gram tissue in the burn eschar and up to $10^4$ bacteria/gram tissue in the remaining post-excision wound bed. The delayed group also demonstrated graft loss in 3 patients and sepsis in 2 patients after surgery[16].

Standard tangential excision of burns requires removal of all "unhealthy" appearing tissue (e.g., brownish fat or blood-stained tissues) down to uniformly bright yellow fat and briskly bleeding vessels[24]. Barret et al.'s findings indicate that it is that it is practically impossible to "sterilize" colonized burn wound bed prior to grafting and that because of current limitations in topical antimicrobials at controlling infection, any significant delay in burn wound excision can significantly impact the degree of skin graft viability. Even more importantly, increased bacteria in delayed excision burn wounds may significantly increase the amount and depth of tissue that needs tangential excision. For a patient with a small 5% TBSA burn in the anterior mid thigh, delayed excision/wound infection may not represent a significant morbidity. However, for a 50% TBSA burn that involves bilateral lower and upper extremities, delayed excision/infection can have tremendous functional consequences if deep tissue excision to remove nonviable, bacteria invaded tissue results in significant exposure of tendons in the leg (e.g., Achilles, tibialis anterior) or in the hand (e.g., extrinsic extensors and flexors) and relatively avascular fascia over joints[24]. Moreover, fascial excision is also associated with increased extremity edema (due to reduced lymphatics), cutaneous denervation with possible sensation loss, and severe cosmetic deformity[24]. In addition, graft loss for a patient with limited donor sites can significantly prolong the time to wound closure—as the donor sites generally require ~2 weeks before healing through re-epithelialization from epidermal appendages such as hair follicles, sebaceous glands, and sweat glands[25]. In addition, to avoid creating a non-healing full-thickness defect that itself would need to be grafted, each donor site can only be used a finite number of times since the dermis and the epithelial appendages in the dermis do not regenerate. Lastly, delayed wound closure, wound infection, and possibly even wound colonization can significantly increase the incidence of hypertrophic scarring—which can cause major negative long term functional and cosmetic sequelae[26-31]. Thus, controlling burn wound infection is critical to short term goals of minimizing septic complications, maximizing tissue salvage and wound closure success as well as long term goals of minimizing hypertrophic scarring/contractures and maximizing function.

Although early excision (within 24 hours) decreases bacteria colonization and improves wound closure outcomes 16, early excision may not be practical in patients that are not medically stable or in burns that are still converting (i.e., premature excision of all burned areas, including indeterminate 2nd degree burns, may result in tissue overexcision). This indicates that better infection control is critical for every day that definitive burn excision/closure therapy is delayed for medical or logistical reasons.

Because systemic antibiotics do not prevent burn wound cellulitis or sepsis[11,18,19], topical antimicrobials and early wound debridement are first line defenses against invasive burn wound pathogens. The topical antimicrobial should form a protective bacteriostatic/bacteriocidal zone against deeper bacteria colonization or invasion. An ideal topical antimicrobial would exhibit the following: 1) good tissue penetration; 2) broad antimicrobial activity without encouraging drug resistance; 3) minimal local/systemic toxicity or side effects; 4) easy, infrequent application; 5) relatively pain free once applied. No current antimicrobial exhibits all the ideal properties and Table 2 summarizes the advantages/disadvantages of commonly used topical antimicrobials.

Historically, silver nitrate ($AgNO_3$) was the first topical agent employed to delay burn eschar colonization in 1964 with the bactericidal component being cationic silver ($Ag^+$)[11,20]. Initial use at a 10% solution was found to exhibit keratinocyte and fibroblast toxicity and current use is limited to 0.5% solutions[11].

Disadvantages include total lack of eschar penetration, systemic effects (electrolyte imbalances), and adverse local effects (tissue staining)[11,20,34]. Although the exact bacteriostatic mechanism of mafenide is still not known[35], it was developed at the US Army Surgical Research Unit (Fort Sam Houston, Tex.) and tested on humans in 1964[33]. It is the only topical antimicrobial with significant eschar penetration due to mafenide's hydrophilic nature[36]. Disadvantages of MA cream include bacteriostatic rather than bactericidal activity, rapid tissue clearance (related to hydrophilic nature), metabolic acidosis[11,20,34], and pain following application [due to the high osmolarity (2000 mOsm/kg) of the cream][37]. The 5% MA solution was FDA approved as an orphan drug in 1998[33], exhibits similar antimicrobial and eschar penetration properties as the cream, but is significantly less painful due to lower osmolarity (340-500 mOsm/kg)[35,37]. To improve fungal coverage, 5% MA is often mixed with Nystatin powder (final 10,000 U/ml Nystatin)[20,38]. The limitations of silver nitrate and MA led to development of silver sulfadiazine (SSD) in 1968[33]. SSD, a complex of sulfadiazine+silver nitrate with antimicrobial activity from the silver as well as the sulfonamide component, is the most commonly used topical burn antimicrobial[20,39]. Disadvantages of SSD include poor eschar

TABLE 2

Commonly Used Burn Topical Antimicrobials

| Agent | Advantages | Disadvantages |
|---|---|---|
| 0.5% Silver nitrate solution Introduced in 1964 | Bactericidal against most gram positives, gram negatives and yeast Avoids mucopurulent exudate formation (pseudoeschar) Minimal pain after application No hypersensitivity | No eschar penetration Electrolyte imbalance (hypotonic solution depletes wound cations) Needs frequent application Discolors wound bed Possible methmeglobinemia Rare silver toxicity |
| Mafenide acetate - historically 11.1% in water-soluble cream, but newer formulation is 8.5% First introduced in 1964 | Bacteriostatic against most gram positives, gram negatives; may be more effective for clostridial and pseudomonal infections than silver nitrate or SSD Good eschar penetration | Potential loss of bacteriostatic action at high (>$10^6$) bacterial loads Effective concentration in eschar drops below therapeutic levels after 10 hours - needing twice daily application Metablic acidosis [drug and metabolite (p-carboxybenzenesulfonamide) inhibit carbonic anhydrase - can worsen ventilation] Pain after application Potential hypersensitivity |
| 1% Silver sulfadiazine (SSD) water soluble cream Developed in 1968 | Bactericidal against most gram positives and some gram negatives Minimal pain after application | Less activity against certain gram negatives (*Enterobacter, Pseudomonas*) and yeast Poor eschar penetration Forms pseudoeschar that requires daily washings Neutropenia[A] Potential hypersensitivity to sulfa component Rare silver toxicity |
| Mafenide acetate - 5% solution First introduced in 1971 | (Similar to cream) Less pain after application vs. cream | (Similar to cream) Effective concentration in eschar drops below therapeutic levels after 6-8 hours - needing 3x-4x daily application |
| Acticoat Rayon/polyester core encased in dense polyethylene mesh coated with nanocrystalline silver. | Bactericidal against most gram positives, gram negatives and fungus Sustained silver release for 3-7 d Minimizes pain from daily dressings | Poor eschar penetration Requires maintenance of moist dressings for silver release Rare silver toxicity |

Table information modified and compiled from the following references: Cioffi et al.[12], D'Avignon et al.[11], Tredget et al.[20], Martineau and Davis[32], Barillo[33]
[A]Neutropenia thought to be due to transient depression of granulocyte-macrophage progenitor cells in the marrow[11].

penetration, less effective gram negative activity, and neutropenia[20,34]. Acticoat is a novel nanocrystalline silver complex with broad antimicrobial properties that also releases silver cations[20]. Disadvantages also include poor eschar penetration[20].

It is clear that burn wound sepsis is still common despite topical antimicrobial use[11]. The early vs. late excision wound colonization data from Barret et al.[16] reinforces the finding that current antimicrobials do not provide a protective buffer zone that effectively controls colonization/invasion of viable subeschar tissue. Treatment failures can occur under several scenarios: 1) bacterial penetration into the eschar exceeds the penetration capacity of commonly used antimicrobials such as SSD, Acticoat, or silver nitrate; 2) effective bacteriostatic/bacteriocidal tissue drug levels cannot be maintained despite initial drug penetration by MA-based topicals; and 3) true bacterial drug resistance to topical agents. True bacterial resistance in this context means that the same bacteria, when taken out of an in vivo wound environment without protective matrices or biofilms, will continue to exhibit drug resistance in vitro. Fortunately, true bacterial resistance for certain silver based antimicrobials is rare[40] and bacteriostatic resistance to MA relatively uncommon[41].

With respect to silver, it's action as an antiseptic may contribute to the rarer incidence of bacterial resistance[40]. Antiseptics are short-acting, broad spectrum agents that nonselectively target cellular activities in both human and bacterial cells—and as such, cannot be given systemically due to excessive toxicity. Antiseptics are less likely to promote bacterial resistance because of their relatively rapid and broad anti-cellular activities[42]. In contrast, antibiotics bind specific bacteria chemical targets that do not exist in humans, and are thus less cytotoxic to human cells than bacterial cells. However, antibiotic binding specificity, while desirably limiting toxicity, also narrows the bacterial species and strain susceptibility to a given antibiotic—and contributes significantly to antibiotic resistance[42]. The current prevalence of multi-antibiotic resistant organisms has renewed interest in the use of the antiseptic silver as an effective, but relatively less toxic antimicrobial[42].

The antimicrobial properties of silver have long been recognized. It has been used for centuries in water recycling and sanitization and for treatment of wound infections[43,44]. In 1884, a German obstetrician introduced silver nitrate application to newborn eyes to prevent gonorrheal infection[44]. In the early 20$^{th}$ century surgeon, William S. Halstead, used silver foil as wound dressings[44]. With the development of modern antibiotics, silver use for infection control declined significantly; however, beginning the late 1960s, silver experienced wide use in cutaneous wounds, most notably, as evident in the preceding paragraphs, in burn care[43]. Modern silver use includes silver based dressings in the form of creams, foams, hydrogels, hydrocolloids, polymeric films, and meshes[43]. In addition, silver is used to reduce bacterial colonization/infection in a broad range of devices such as vascular and urinary catheters[43], endotracheal tubes, and implantable prostheses[46]. However, it is difficult to directly extrapolate published literature on silver toxicity to this present study. This is because different forms of silver reservoir (e.g. silver salts such as AgNO$_3$, silver compounds such as silver sulfadiazine, or nanocrystalline silver) have different profiles of silver release and bioactivity[47]. Even within one reservoir category of nanocrystalline silver, there is tremendous variation in particle size, particle aggregation, concentration or coating thickness (in implants), rate of release from implants or surfaces, and the solution used when studying release rates. From the extensive skin literature on silver use, general agreement exists that silver can be toxic to keratinocytes in vitro[47], but in vivo studies disagree on whether actual keratinocyte reepithelialization is decreased[48] or increased[49]. Moreover, Tian et al. showed more rapid healing and less scar after addition of silver nanoparticles in mouse wounds[50]. Thus, in vitro studies may overestimate in vivo cytotoxicity[51].

Both silver nitrate and nanosilver materials achieve their antimicrobial activity by generation and/or release of cationic silver (Ag$^+$) [i.e., ionic silver Ag (1)]; however, they may differ in the reservoir form for the active silver ions[42]. For instance, the reservoir form for AgNO$_3$ is a chemical combination of silver and nitrate, while the reservoir form for Acticoat are silver nanoparticles (Ag$^{NANO}$). Non-nanoscale elemental silver [Ag (0)] used in silverware and jewelry is relatively insoluble in most fluids, and hence there is minimal oxidative Ag$^+$ release[42]. In contrast, because nanoscale particles have relatively large surface to mass ratio, they exhibit much more solubility and chemical reactivity, and hence much higher oxidative Ag$^+$ release and/or much higher formation of partially oxidized silver nanoparticles with chemisorbed (surface bound) Ag$^{+52}$. In general, silver nanoparticles<50 nm are believed to exhibit more satisfacgtory antimicrobial activity[52,53].

Mechanistically, Ag$^+$ is thought to attach to specific thiol groups containing sulfur and hydrogen found in a variety of structural and functional bacterial proteins[42]. Because of this, Ag$^+$ can bind and disrupt multiple components of bacterial structure/metabolism including: cell wall components, cellular transport and enzyme systems such as the respiratory cytochromes, DNA and RNA processes to prevent cell division and transcription[43]. Bacterial resistance to silver, although described and some of the genetic basis elucidated[44], may be less likely than resistance to antibiotics as bacterial survival would require at least three separate mutations in three different bacterial systems—all within one generation of bacteria[43].

Overall, nanoscale silver is believed to be a more effective antimicrobial than silver nitrate because: 1) the solution rate of active Ag$^+$ from Ag$^{NANO}$ is greater than the inactivation rate of Ag$^+$ by serum proteins, making it possible to achieve higher and more sustained mean inhibitory concentrations (MIC)[54] (i.e., better Ag$^+$ reservoir) and 2) increased bactericidal activity deriving from released Ag$^+$ as well as Ag$^{NANO}$ particles[53] exhibiting chemisorbed surface Ag$^{+52}$. In support of this, in vitro time kill-kinetic assays demonstrated good antimicrobial activity for Acticoat against fungal subspecies (e.g., *Candida albicans* or glabrata as well as *Mucor* and *Aspergillus*), while silver nitrate and SSD demonstrated activity for only *C. albicans*[40]. These results indicate that silver bactericidal activity can vary depending on the form of silver used and that current nanosilver formulations can exhibit significant broad antimicrobial activity. However, variable release rates depending on dressing hydration[55] and inadequate tissue penetration are still significant issues.

With respect to MA, although it is bacteriostatic, its ability to penetrate rapidly into tissues and relatively low incidence of documented resistance can be important for short term treatment of open wounds. Using zone of inhibition assays, Kucan et al. found that 5% MA was effective against all 43 different *A. baumannii* strains collected from service members injured in Irag and Afghanistan[56]. Kucan et al. also cited no evidence of resistance in over 11,000 strains of *P. aeruginosa* collected over 25 years at the US Army Institute of Surgical Research[56]. Using a similar type inhibition zone assay, Gallant-Behm et al. also found good 5% MA activity against *S. aureus*, MRSA, and most gram negatives including P. aeruginosa, but no activity against vancomycin resistant Enterococcus (VRE), Burkholderia cepacia, E. coli, or any fungal species[40]. These results indicate that the significant benefits associated with increased MA penetration are somewhat offset by its limited antimicrobial spectrum.

Mafentide tissue permeability studies were originally performed by Harrison et al. who analyzed absorption of $^{14}$C-labeled MA through burned rat and human skin[57]. The high water solubility and low plasma protein affinity of 11.2% MA cream permits rapid burned tissue penetration with a peak concentration of 1 mg/100 g tissue within 30 minutes. However, rapid tissue penetration of MA is also associated with relatively rapid tissue clearance—and relatively rapid drop in effectively bacteriostatic local tissues concentrations. Thus, strategies to enhance mafenide retention in burn wounds may increase the antimicrobial effectiveness of MA as well as potentially decrease the total dose (with respect to concentration and application frequency) and thus minimize systemic toxicity (e.g., metabolic acidosis). Taken as a whole, these observations indicate that adequate tissue penetration, adequate tissue delivery (i.e., ability to maintain sustained tissue drug levels), and microorganism susceptibility are critical to maximizing antimicrobial activity.

Timely debridement of all devitalized tissue is critical to infection control in both burns and other injuries. For cases where the wound bed is well vascularized and the TBSA needing coverage does not exceed the amount of autograft skin available, STSG can be applied and the wound closed in one stage. However, for burn cases with insufficient autograft donor skin, other forms of permanent or temporary wound coverage are required.

For permanent wound coverage, the only alternative to conventional meshed autograft skin are cultured epithelial autografts (CEA). CEA use however is hampered by tremendous costs, need for 3 week culture period, long term fragility manifesting as recurrent open wounds, and increased rate of burn scar contractures requiring more reconstructive procedures[58].

For temporary coverage, allograft skin, xenograft skin, or Integra-DRT (Integra LifeSciences Inc., Plainsboro, N.J.) can be applied. Allograft advantages are its ability to be revascularized by the recipient wound bed, resulting in increased graft adherence and better infection control[39]. Disadvantages are need for reapplication every 2 weeks due to rejection and possible disease transmission. In addition, because initial allograft skin (as well as autograft) survival depends on imbibition (net diffusion of plasma into graft), followed by inosculation (growth of recipient endothelial cells into pre-existing donor capillary tubes)[59,60], allograft cannot be placed over areas with significant (>1 cm$^2$) non-vascularized tissue (e.g., bone devoid of periosteum, tendon devoid of paratenon, open joints)[61]. Porcine dermal xenografts are further disadvantaged by less adherence and protection from desiccation and infection than allograft due to lack of revascularization by the recipient wound bed resulting in degenerative necrosis and need for frequent reapplication[39].

Integra-DRT is a bilayer membrane in which the inner, dermal replacement layer is made of a porous matrix of crosslinked bovine tendon collagen fibers and a glycosaminoglycan (chondroitin-6-sulfate) that is manufactured with a controlled porosity and defined degradation rate; the outer layer is a polysiloxane polymer that functions as a temporary epidermis[24,62]. Integra-DRT is acellular and nonviable when grafted but is incorporated and vascularized by viable tissue underneath and adjacent the Integra-DRT[61]. Once incorporated, a thin epidermal autograft (0.004-0.006 inches) can then be grafted over Integra-DRT for definitive closure. Integra-DRT advantages include ability to induce tissue ingrowth over poorly-vascularized, but viable, wound bed areas (e.g., exposed bone, tendon, joint)[61]. Disadvantages include need for two-step surgery process before final wound closure, increased infection rates, and prolonged times for adequate ingrowth/angiogenesis into Integra-DRT. Cited infection rates ranged from 0 to 55% from multiple Integra sponsored trials in the Product Information Sheet. This rate is consistent with other published reports in the literature ranging from about 0-30% despite application of topical antimicrobials[61,63-65]. With respect to tissue incorporation, the Product Information Sheet recommends 14-21 days before epidermal autograft placement.

It has been observed that the 1.5-2 mm thick Integra-DRT[66] is usually vascularized in 2 to 3 weeks when relying on direct vertical ingrowth from the recipient wound bed. But in cases where Integra-DRT is grafted over non- or poorly vascularized structures, incorporation is dependent on initial vertical ingrowth (in areas where Integra-DRT is in contact with vascularized wound bed) and then horizontal or radial ingrowth through the Integra-DRT (in areas where Integra-DRT is in contact with a non vascularized wound bed). Depending on the total area of non-vascularized wound bed, incorporation can take as long as 6-8 weeks[61]. Interestingly, use of a negative pressure wound therapy device (vacuum-assisted closure device-VAC; KCI Inc., San Antonio, Tex.) over Integra-DRT appears to both reduce the incidence of infection (range 0-12.5%)[63-65] and time to definitive autograft wound closure (mean time to grafting was 10 days by Jeschke et al.[64] and 7.25 days by Molnr et al.[65] This suggests that interventions promoting tissue ingrowth can decrease the time to Integra-DRT incorporation and possibly decrease the incidence of Integra-DRT infection. However, burn patients may not have enough intact, non-injured skin for VAC application.

It is clear that current burn wound coverage is still largely dependent on autograft skin. Requirement for successful autograft survival include low wound bioburden and good recipient bed vascularization[59]. Thus strategies to promote infection control and tissue ingrowth may help autograft mediated wound closure success rates—especially in wound beds with large bioburdens even after adequate resection (i.e., as discussed in Barret et al. noted autograft loss in 3 out of 8 patients in the delayed excision group with high wound bioburden[16]). In addition, promoting infection control and tissue ingrowth may also reduce infection rates during Integra-DRT incorporation as well as allow for faster skin grafting over Integra-DRT—thereby decreasing the overall wound closure time. Lastly, decreased autograft or Integra treatment failures can reduce the need for reoperation, resulting in significant time and cost savings. Thus, therapies that promote fibroblast migration and vascular ingrowth with concomitant antimicrobial activity are required to increase the efficacy and efficiency of present skin closure methods.

The embodiments of the present invention address these concerns as well as others that are apparent by one having ordinary skill in the art.

SUMMARY OF THE INVENTION

In one aspect, the present invention provides a transcutaneous multimodal delivery device (TMDS). The TMDS comprises a transcutaneous drug delivery (TDD) component and a sustained delivery and retention (SDR) component. The TMDS provides a controlled delivery of at least one active agent comprising a first therapeutic drug and a second therapeutic drug where the first therapeutic drug and the second therapeutic drug are the same or different. The TDD component comprises dissovable microneedles having a dimension so as to allow the microneedles to penetrate eschar of skin without reaching viable tissue, and the SDR component comprises a release control vehicle to provide a controlled release of the first therapeutic drug or the second therapeutic drug.

In some embodiments of the invention TMDS, at least one of the first therapeutic drug and the second therapeutic drug is an antimicrobial agent.

In some embodiments of the invention TMDS, at least one of the first therapeutic drug and the second therapeutic drug is a biologically active agent.

In some embodiments of the invention TMDS, the antimicrobial agent is silver nitrate, nanoparticulate silver ($Ag^{nano}$), mafenide acetate (MA), iodine, and silver sulfadiazine (SDD); and the biologically active agent is platelet derived growth factor (PDGF) or a cell encapsulated within the release control vehicle.

In some embodiments of the TMDS of invention, the dissolvable microneedles comprise a sharp tip and a blunt tip and completely dissolve within a period ranging from about 10 seconds to about 10 days upon application to a patient. For example, the dissolvable microneedles completely dissolve within 30 seconds, 30 minutes, 1 hr, 2 hr, 5 hr, 10 hr, 24 hr, 2 days, 5 days, or 10 days upon application to a patient. In some embodiments, the microneedles comprise a sharp tip capable of complete dissolution within about 1 hr upon application to a patient.

In the various embodiments of the TMDS of invention, the release control vehicle provides a sustained release of the first therapeutic drug or the second therapeutic drug over a period up to 30 days.

In the various embodiments of the TMDS of invention, the dissolvable microneedles are formed from a material comprising a dissolvable polymer. Examples of dissolvable polymer can be, e.g., carboxylmethyl cellulose (CMC), a derivative of CMC, hydroxypropyl methylcellulose phthalate (HPMCP), a derivative of HPMCP, or a combination thereof.

In the various embodiments of the TMDS of invention, the release control vehicle comprises a biodegradable polymer. Examples of biodegradable polymer can be, e.g., hyaluronic acid (HA), a derivative of HA, collagen, or a derivative of collagen, or a combination thereof.

In the various embodiments of the TMDS of invention, the release control vehicle comprises a targeting ligand Y for targeted delivery of the first therapeutic drug or the second therapeutic drug; and wherein the targeting ligand Y is attached to any of the following:

surface of liposomes of phospholipid bilayer where the first therapeutic drug or the second therapeutic drug is associated within the bilayer and the hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

In another aspect, the present invention provides a method of treating or ameliorating a skin condition or non-skin condition, the method comprising applying to a patient having the skin condition a transcutaneous multimodal delivery device (TMDS) that comprises a transcutaneous drug delivery (TDD) component and a sustained delivery and retention (SDR) component. The skin condition is wounded skin or diseased skin. Examples of such wounded skin or diseased skin are burn wound and other non-healing or infected cutaneous wounds, e.g., chronic diabetic ulcers and necrotizing fasciits. Examples of non-skin condition can be, but are not limited to, muscle injury, bone injury, or cartilage injury.

In some embodiments of the method of invention, at least one of the first therapeutic drug and the second therapeutic drug is an antimicrobial agent.

In some embodiments of the method of invention, at least one of the first therapeutic drug and the second therapeutic drug is a biologically active agent.

In some embodiments of the method of invention, the antimicrobial agent is silver nitrate, nanoparticulate silver ($Ag^{nano}$), mafenide acetate (MA), iodine, and silver sulfadiazine (SDD); and the biologically active agent is platelet derived growth factor (PDGF) or a cell encapsulated within the release control vehicle.

In some embodiments of the method of invention, the dissolvable microneedles comprise a sharp tip and a blunt tip and completely dissolve within a period ranging from about 10 seconds to about 10 days upon application to a patient. For example, the dissolvable microneedles completely dissolve within 30 seconds, 30 minutes, 1 hr, 2 hr, 5 hr, 10 hr, 24 hr, 2 days, 5 days, or 10 days upon application to a patient. In some embodiments, the microneedles comprise a sharp tip capable of complete dissolution within about 1 hr upon application to a patient.

In some embodiments of the method of invention, the release control vehicle provides a sustained release of the first therapeutic drug or the second therapeutic drug over a period up to 30 days.

In some embodiments of the method of invention, the dissolvable microneedles are formed from a material comprising a dissolvable polymer. Examples of dissolvable polymer can be, e.g., carboxylmethyl cellulose (CMC), a derivative of CMC, hydroxypropyl methylcellulose phthalate (HPMCP), a derivative of HPMCP, or a combination thereof.

In the various embodiments of the method of invention, the release control vehicle comprises a targeting ligand Y for targeted delivery of the first therapeutic drug or the second therapeutic drug; and wherein the targeting ligand Y is attached to any of the following:

surface of liposomes of phospholipid bilayer where the first therapeutic drug or the second therapeutic drug is associated within the bilayer and the hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

In some embodiments of the method of invention, the release control vehicle comprises a biodegradable polymer. Examples of biodegradable polymer can be, e.g., hyaluronic acid (HA), a derivative of HA, collagen, or a derivative of collagen, or a combination thereof.

In a further aspect, the invention provides a method of fabricating a transcutaneous multimodal delivery device (TMDS), the method comprising:

forming a transcutaneous drug delivery (TDD) component;

forming a sustained delivery and retention (SDR) component; and forming the TMDS, wherein the TMDS provides a controlled delivery of at least one active agent comprising a first therapeutic drug and a second therapeutic drug where the first therapeutic drug and the second therapeutic drug is the same or different;

wherein the TDD component comprises dissovable microneedles having a dimension so as to allow the microneedles to penetrate eschar of skin without reaching viable tissue, and wherein the SDR component comprises a release control vehicle to provide a controlled release of the first therapeutic drug or the second therapeutic drug.

In some embodiments of invention method of fabrication, at least one of the first therapeutic drug and the second therapeutic drug is an antimicrobial agent.

In some embodiments of invention method of fabrication, at least one of the first therapeutic drug and the second therapeutic drug is a biologically active agent.

In some embodiments of invention method of fabrication, the antimicrobial agent is silver nitrate, nanoparticulate silver ($Ag^{nano}$), mafenide acetate (MA), iodine, and silver sulfadiazine (SDD); and the biologically active agent is platelet derived growth factor (PDGF) or a cell encapsulated within the release control vehicle.

In some embodiments of invention method of fabrication, the dissolvable microneedles comprise a sharp tip and a blunt tip and completely dissolve within a period ranging from about 10 seconds to about 10 days upon application to a patient. For example, the dissolvable microneedles completely dissolve within 30 seconds, 30 minutes, 1 hr, 2 hr, 5 hr, 10 hr, 24 hr, 2 days, 5 days, or 10 days upon application to a patient. In some embodiments, the microneedles comprise a sharp tip capable of complete dissolution within about 1 hr upon application to a patient.

In some embodiments of invention method of fabrication, the release control vehicle provides a sustained release of the first therapeutic drug or the second therapeutic drug over a period up to 30 days.

In some embodiments of invention method of fabrication, the dissolvable microneedles are formed from a material comprising a dissolvable polymer. Examples of dissolvable polymer can be, e.g., carboxylmethyl cellulose (CMC), a derivative of CMC, hydroxypropyl methylcellulose phthalate (HPMCP), a derivative of HPMCP, or a combination thereof.

In some embodiments of invention method of fabrication, the release control vehicle comprises a biodegradable polymer. Examples of biodegradable polymer can be, e.g., hyaluronic acid (HA), a derivative of HA, collagen, or a derivative of collagen, or a combination thereof.

In the various embodiments of the method of invention, the release control vehicle comprises a targeting ligand Y for targeted delivery of the first therapeutic drug or the second therapeutic drug; and wherein the targeting ligand Y is attached to any of the following:

surface of liposomes of phospholipid bilayer where the first therapeutic drug or the second therapeutic drug is associated within the bilayer and the hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

BRIEF DESCRIPTION OF DRAWINGS

FIG. 10A shows that the TDD component can two subcomponents, one component being sharp tips and the other one blunt tips and a base layer. FIG. 10B shows that the SDR component can comprise release control vehicles, which are microspheres and nanospheres comprising biopolymer or bioceramic with plasticizer and the active agent. The active agent can be proteins, peptides, small molecular weight siRNA, AS-ODNs, and DNA.

DETAILED DESCRIPTION

Figure 1:
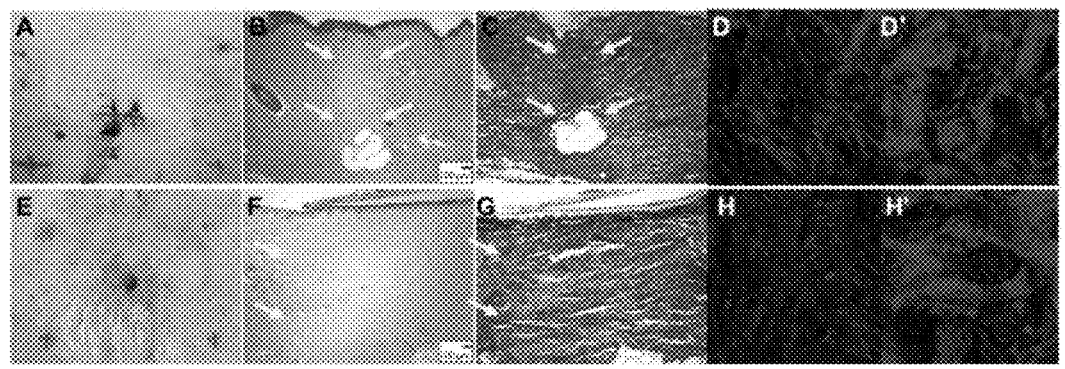
FIG. 1 shows porcine models of cutaneous wound healing. A. Porcine full-thickness primary intention healing model. Sutured 1.5 cm wound immediately after surgery. B. Hematoxylin & Eosin (H&E) stained sections at 4 weeks (green arrows demarcate wound site), 40×. C. Picrosirius red (PSR) collagen staining (green arrows demarcate wound site), 40×. D. Confocal image of dermal scar and corresponding unwounded dermis (D'), 630×. E. Porcine full-thickness secondary intention healing model. 5-mm punch biopsies immediately after surgery, covered in adherent wound dressing. F. H&E at 4 weeks (yellow arrows demarcate wound site), 40×. G. PSR collagen staining (yellow arrows demarcate wound site), 40×. H. Confocal image of dermal scar and corresponding unwounded dermis (H'), 630×.

In one aspect, the present invention provides a transcutaneous multimodal delivery device (TMDS). The TMDS comprises a transcutaneous drug delivery (TDD) component and a sustained delivery and retention (SDR) component. The TMDS provides a controlled delivery of at least one active agent comprising a first therapeutic drug and a second therapeutic drug where the first therapeutic drug and the second therapeutic drug are the same or different. The TDD component comprises dissovable microneedles having a dimension so as to allow the microneedles to penetrate eschar of skin without reaching viable tissue, and the SDR component comprises a release control vehicle to provide a controlled release of the first therapeutic drug or the second therapeutic drug.

In some embodiments of the invention TMDS, at least one of the first therapeutic drug and the second therapeutic drug is an antimicrobial agent.

In some embodiments of the invention TMDS, at least one of the first therapeutic drug and the second therapeutic drug is a biologically active agent.

In some embodiments of the invention TMDS, the antimicrobial agent is silver nitrate, nanoparticulate silver ($Ag^{nano}$), mafenide acetate (MA), iodine, and silver sulfadiazine (SDD); and the biologically active agent is platelet derived growth factor (PDGF) or a cell encapsulated within the release control vehicle.

In some embodiments of the TMDS of invention, the dissolvable microneedles comprise a sharp tip and a blunt tip and completely dissolve within a period ranging from about 10 seconds to about 10 days upon application to a patient. For example, the dissolvable microneedles completely dissolve within 30 seconds, 30 minutes, 1 hr, 2 hr, 5 hr, 10 hr, 24 hr, 2 days, 5 days, or 10 days upon application to a patient. In some embodiments, the microneedles comprise a sharp tip capable of complete dissolution within about 1 hr upon application to a patient.

In the various embodiments of the TMDS of invention, the release control vehicle provides a sustained release of the first therapeutic drug or the second therapeutic drug over a period up to 30 days.

In the various embodiments of the TMDS of invention, the dissolvable microneedles are formed from a material comprising a dissolvable polymer. Examples of dissolvable polymer can be, e.g., carboxylmethyl cellulose (CMC), a derivative of CMC, hydroxypropyl methylcellulose phthalate (HPMCP), a derivative of HPMCP, or a combination thereof.

In the various embodiments of the TMDS of invention, the release control vehicle comprises a biodegradable polymer. Examples of biodegradable polymer can be, e.g., hyaluronic acid (HA), a derivative of HA, collagen, or a derivative of collagen, or a combination thereof.

In the various embodiments of the TMDS of invention, the release control vehicle comprises a targeting ligand Y for targeted delivery of the first therapeutic drug or the second therapeutic drug; and wherein the targeting ligand Y is attached to any of the following:

surface of liposomes of phospholipid bilayer where the first therapeutic drug or the second therapeutic drug is associated within the bilayer and the hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

In another aspect, the present invention provides a method of treating or ameliorating a skin condition or non-skin condition, the method comprising applying to a patient having the skin condition a transcutaneous multimodal delivery device (TMDS) that comprises a transcutaneous drug delivery (TDD) component and a sustained delivery and retention (SDR) component. The skin condition is wounded skin or diseased skin. Examples of such wounded skin or diseased skin are burn wound and other non-healing or infected cutaneous wounds, e.g., chronic diabetic ulcers and necrotizing fasciits. Examples of non-skin condition can be, but are not limited to, muscle injury, bone injury, or cartilage injury.

In some embodiments of the method of invention, at least one of the first therapeutic drug and the second therapeutic drug is an antimicrobial agent.

In some embodiments of the method of invention, at least one of the first therapeutic drug and the second therapeutic drug is a biologically active agent.

In some embodiments of the method of invention, the antimicrobial agent is silver nitrate, nanoparticulate silver ($Ag^{nano}$), mafenide acetate (MA), iodine, and silver sulfadiazine (SDD); and the biologically active agent is platelet derived growth factor (PDGF) or a cell encapsulated within the release control vehicle.

In some embodiments of the method of invention, the dissolvable microneedles comprise a sharp tip and a blunt tip and completely dissolve within a period ranging from about 10 seconds to about 10 days upon application to a patient. For example, the dissolvable microneedles completely dissolve within 30 seconds, 30 minutes, 1 hr, 2 hr, 5 hr, 10 hr, 24 hr, 2 days, 5 days, or 10 days upon application to a patient. In some embodiments, the microneedles comprise a sharp tip capable of complete dissolution within about 1 hr upon application to a patient.

In some embodiments of the method of invention, the release control vehicle provides a sustained release of the first therapeutic drug or the second therapeutic drug over a period up to 30 days.

In some embodiments of the method of invention, the dissolvable microneedles are formed from a material comprising a dissolvable polymer. Examples of dissolvable polymer can be, e.g., carboxylmethyl cellulose (CMC), a derivative of CMC, hydroxypropyl methylcellulose phthalate (HPMCP), a derivative of HPMCP, or a combination thereof.

In the various embodiments of the method of invention, the release control vehicle comprises a targeting ligand Y for targeted delivery of the first therapeutic drug or the second therapeutic drug; and wherein the targeting ligand Y is attached to any of the following:

surface of liposomes of phospholipid bilayer where the first therapeutic drug or the second therapeutic drug is associated within the bilayer and the hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

In some embodiments of the method of invention, the release control vehicle comprises a biodegradable polymer. Examples of biodegradable polymer can be, e.g., hyaluronic acid (HA), a derivative of HA, collagen, or a derivative of collagen, or a combination thereof.

In a further aspect, the invention provides a method of fabricating a transcutaneous multimodal delivery device (TMDS), the method comprising:

forming a transcutaneous drug delivery (TDD) component;

forming a sustained delivery and retention (SDR) component; and forming the TMDS, wherein the TMDS provides a controlled delivery of at least one active agent comprising a first therapeutic drug and a second therapeutic drug where the first therapeutic drug and the second therapeutic drug is the same or different;

wherein the TDD component comprises dissovable microneedles having a dimension so as to allow the microneedles to penetrate eschar of skin without reaching viable tissue, and wherein the SDR component comprises a release control vehicle to provide a controlled release of the first therapeutic drug or the second therapeutic drug.

In some embodiments of invention method of fabrication, at least one of the first therapeutic drug and the second therapeutic drug is an antimicrobial agent.

In some embodiments of invention method of fabrication, at least one of the first therapeutic drug and the second therapeutic drag is a biologically active agent.

In some embodiments of invention method of fabrication, the antimicrobial agent is silver nitrate, nanoparticulate silver ($Ag^{nano}$), mafenide acetate (MA), iodine, and silver sulfadiazine (SDD); and the biologically active agent is platelet derived growth factor (PDGF) or a cell encapsulated within the release control vehicle.

In some embodiments of invention method of fabrication, the dissolvable microneedles comprise a sharp tip and a blunt tip and completely dissolve within a period ranging from about 10 seconds to about 10 days upon application to a patient. For example, the dissolvable microneedles completely dissolve within 30 seconds, 30 minutes, 1 hr, 2 hr, 5 hr, 10 hr, 24 hr, 2 days, 5 days, or 10 days upon application to a patient. In some embodiments, the microneedles comprise a sharp tip capable of complete dissolution within about 1 hr upon application to a patient.

In some embodiments of invention method of fabrication, the release control vehicle provides a sustained release of the first therapeutic drug or the second therapeutic drug over a period up to 30 days.

In some embodiments of invention method of fabrication, the dissolvable microneedles are formed from a material comprising a dissolvable polymer. Examples of dissolvable polymer can be, e.g., carboxylmethyl cellulose (CMC), a derivative of CMC, hydroxypropyl methylcellulose phthalate (HPMCP), a derivative of HPMCP, or a combination thereof.

In some embodiments of invention method of fabrication, the release control vehicle comprises a biodegradable polymer. Examples of biodegradable polymer can be, e.g., hyaluronic acid (HA), a derivative of HA, collagen, or a derivative of collagen, or a combination thereof.

In the various embodiments of the method of invention, the release control vehicle comprises a targeting ligand Y for targeted delivery of the first therapeutic drug or the second therapeutic drug; and wherein the targeting ligand Y is attached to any of the following:

surface of liposomes of phospholipid bilayer where the first therapeutic drug or the second therapeutic drug is associated within the bilayer and the hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

As used herein, the term therapeutic drug refers to any therapeutics effective for treating or ameliorating a skin wound of disease. In some embodiments, the term therapeutic drug can be an antimicrobial drug or agent. In some embodiments, the term therapeutic drug can refer to an anti-inflammatory agent. In some further embodiments, the term therapeutic drug can refer to biologic agents such as, but not limited to, antibodies, proteins, peptides, siRNA, anti-sense oligonucleotides, DNA, or cells. Examples of proteins include growth factors such as platelet derived growth factor. Examples of cells include stem cells such as mesenchymal stem cells, adipose derived stem cells, perivascular stem cells, as well as non-stem cells such as epithelial cells.

As used herein, the term release control vehicle refers to a device or carrier in a form capable of providing controlled release of an active agent from a TMDS described herein. The vehicle generally comprises at least one polymeric material and can take the form of, for example, a coating, a drug matrix, microparticles or nanoparticles, microspheres, and microcapsules. The release control vehicle can include one or more of HA, a derivative of HA, collagen, a derivative of collagen, or a biocompatible polymer, which can be biodegradable or biodurable. Examples of biocompatible polymers are described below in more detail.

As used herein, the term release control refers to a TMDS device disclosed herein capable of providing a release profile of an active agent(s) that comprises a fast release profile and a sustained release profile. In some embodiments, the fast release profile can be achieved by the dissolvable TDD component of the TMDS device and the sustained release profile can be achieved by the SDR component of the TMDS device. In some embodiments, the term fast release refers to complete or substantially complete (e.g., release of about 90% or above the total active agent(s)) within a period of 30 minutes, 20 minutes, 10 minutes, 5 minutes, 1 minute, 30 seconds, 20 seconds, or 10 seconds. In some embodiments, a fast release profile where a bioactive agent releases completely or substantially completely within a period of about 30 seconds, 20 seconds, or 10 seconds can be used interchangeably with the term burst release.

In some embodiments, the TDD component has two sub-components. One that is designed to dissolved rapidly (sharp tip 10-30 seconds). The other that is designed to dissolved less rapidly (blunt tip~10-30 min). This is so there is less vascular trauma as the device is being inserted. The sharp tip is designed to penetrate the tissues, the blunt tip is designed to take advantage of the original sharp tip penetration, and then to penetrate further without causing further vascular trauma. The blunt tip can also act as a hemostatic device and hold pressure over any areas in which there is vascular injury by the sharp tip.

In some embodiments, the term sustained release refers to complete or substantially complete (e.g., release of about 90% or above the total active agent(s)) over a period from above 5 days to up to 30 days.

Figure 10:
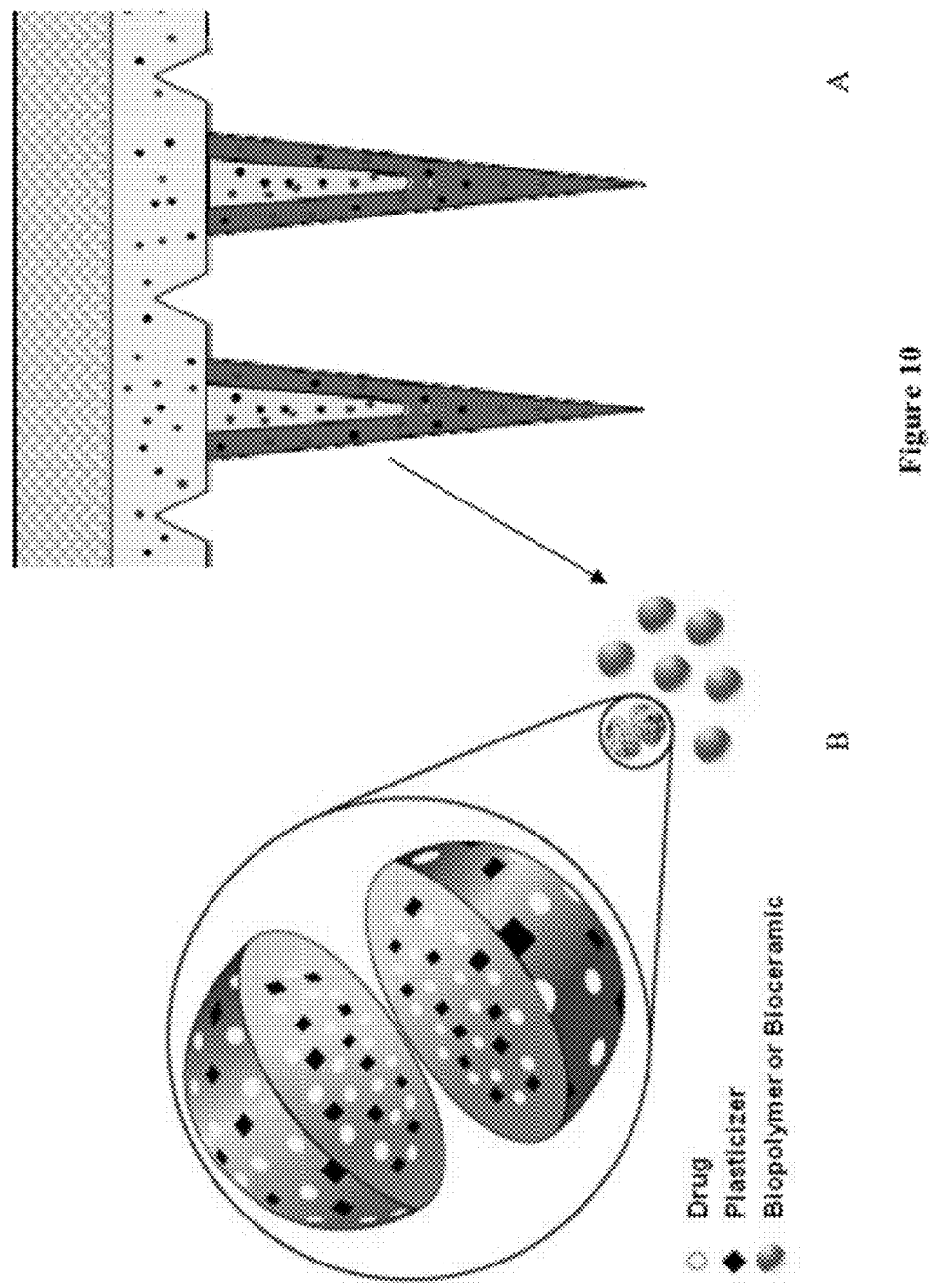
FIG. 10 illustrates an embodiment of the TMDS of invention where release control vehicle in the SDR component using a polymer matrix carrier to achieve controlled drug delivery.

In some embodiments, the release control vehicle provides a release profile of the active agent that can include burst release, sustained release, timed release, release on demand, or a combination thereof. Any of these release profile can be achieved using proper material engineering technologies, which are well established in the art for each of these release profiles (see, e.g., Edith Mathiowitz, Encyclopedia of Controlled Drug Delivery, Wiley, 1999). For example, a polymeric carrier with specific hydrophilicity/hydrophobicity, degradation, and/or phase transition properties sensitive to temperature and pH can be used to trigger or cause a desirable release profile. FIG. 10 illustrates an embodiment of the TMDS of invention where release control vehicle in the SDR component using a polymer matrix carrier to achieve controlled drug delivery. FIG. 10A shows that the TDD component can two subcomponents, one component being sharp tips and the other one blunt tips and a base layer. FIG. 10B shows that the SDR component can comprise release control vehicles, which are microspheres and nanospheres comprising biopolymer or bioceramic with plasticizer and the active agent. The active agent can be proteins, peptides, small molecular weight siRNA, AS-ODNs, and DNA.

Figure 11:
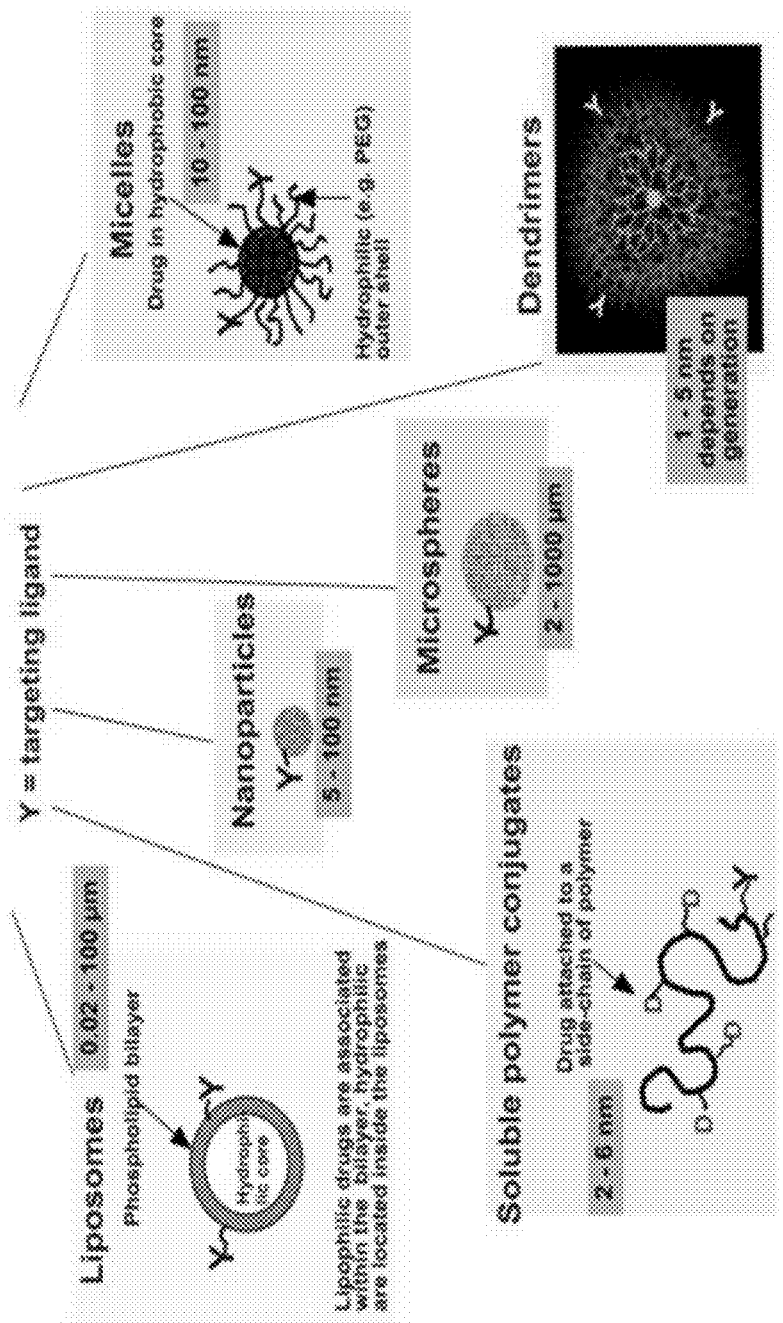
FIG. 11 shows an embodiment of a TMDS device of invention where the SDR component of the TMDS device is used for targeted delivery of an active agent.

FIG. 11 shows an embodiment of a TMDS device of invention where the SDR component of the TMDS device is used for targeted delivery of an active agent. As shown in FIG. 11, in a release control vehicle, a targeting ligand Y can be attached to any of the following:

surface of liposomes of phospholipid bilayer where a hydrophilic drug (e.g., the first therapeutic drug or the second therapeutic drug described above) is associated within the bilayer and the hydrophilic layer is located inside the bilayer as the hydrophilic core;

surface of nanoparticles (e.g., particles having a diameter of 5-100 nm) comprising e.g., the first therapeutic drug or the second therapeutic drug described above;

surface of microparticles (e.g., particles having a diameter of 2-100 microns) comprising e.g., the first therapeutic drug or the second therapeutic drug described above;

surface of micelles (e.g., micelles having a diameter of 10-100 nm) having a hydrophilic outer shell (e.g., a hydrophilic polymer such as PEG) and a hydrophobic core where a drug (e.g., the first therapeutic drug or the second therapeutic drug described above) is located in the hydrophobic core;

surface of dendrimers (e.g., dendrimers having a diameter of 1-5 nm depending on the generation) comprising e.g., the first therapeutic drug or the second therapeutic drug described above; and soluble polymer conjugates (e.g., conjugates having a size of 2-6 nm) where a drug (e.g., the first therapeutic drug or the second therapeutic drug described above) is attached to side chains of polymer.

Figure 12:
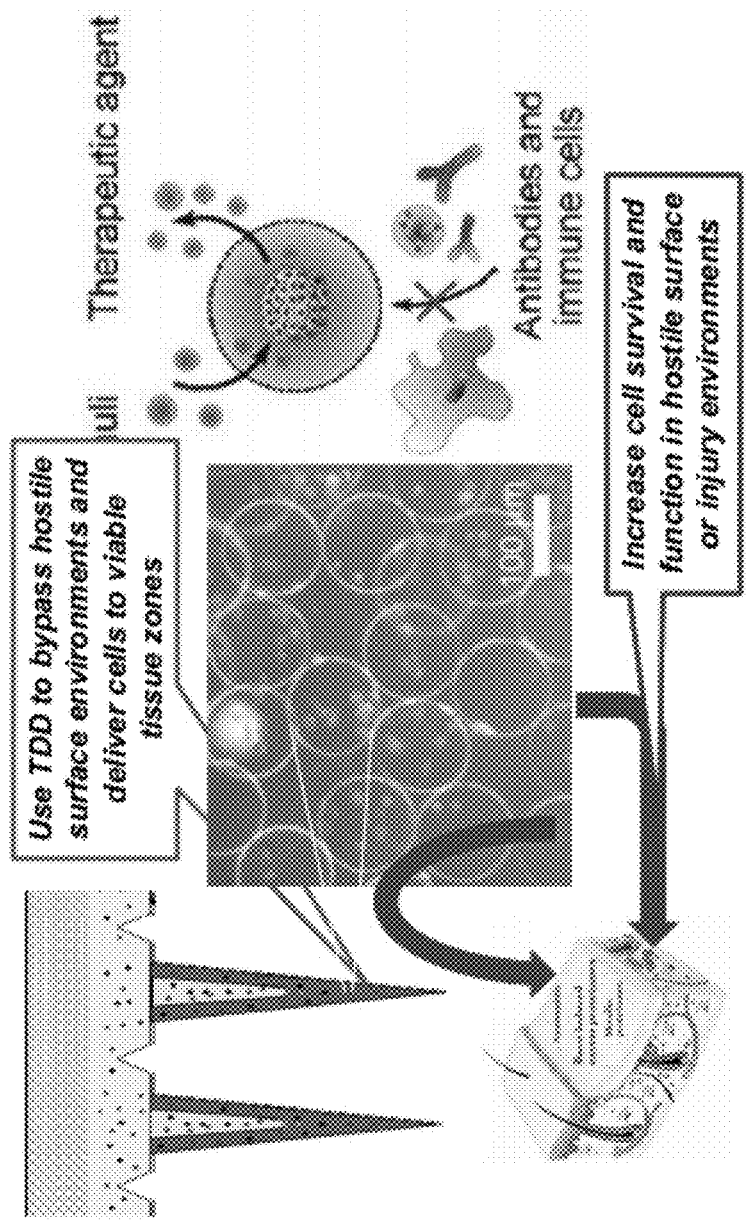
FIG. 12 shows an embodiment of a TMDS device of invention where the TDD component is used to bypass hostile surface environments and deliver cells to viable tissue zones, which results in increased cell survival and function of a therapeutic agent in hostile surface or injury environments, which include a rich population of antibodies and/or immune cells.

FIG. 12 shows an embodiment of a TMDS device of invention where the TDD component is used to bypass hostile surface environments and deliver cells to viable tissue zones, which results in increased cell survival and function of a therapeutic agent in hostile surface or injury environments, which include a rich population of antibodies and/or immune cells.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the skin, the nature of the therapy desired, the time over which the ingredient administered resides at the vascular site, and if other active agents are employed, the nature and type of the substance or combination of substances. Therapeutic effective dosages can be determined empirically, for example by using suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Antimicrobial Agents

The antimicrobial agents useful for the present invention can be any antimicrobial agent in the art of medicine. Such antimicrobial agent generally falls within the categories known as antibiotics, antifungals, antiprotozoals, and antivirals. Examples of antimicrobial agents can be, e.g., silver nitrate, silver particles (e.g., nanosilver $Ag^{nano}$), iodine, mafenide acetate (MA), and silver sulfadiazine (SDD). Other examples of antimicrobial agents include, antibiotics such as gentamycin, vancomycin, or antifungals such as fluconazole, amphotericin.

Dissolvable Polymers

Any dissolvable polymers can be used to fabricate the TDD component described herein. Examples of such polymers include, but are not limited to, poly(ethylene glycol) (PEG), poly(lactide-co-glycolide)-co-poly(ethylene glycol) (PLGA-PEG) block copolymer, other PEG copolymers, poly(vinyl alcohol) (PVA), hyaluronic acid, hydroxyl cellulose, carboxymethylcellulose (CMC), polysaccharides, phosphoryl choline containing polymers, chitosan, collagen, and combinations thereof.

Biocompatible Polymers

In some embodiments, TMDS device can include other biocompatible polymers. The biocompatible polymer can be biodegradable (both bioerodable or bioabsorbable) or nondegradable and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly (isobutyl methacrylate), poly(tert-butyl methacrylate), poly (n-propyl methacrylate), poly(isopropyl methacrylate), poly (ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly (ether ester), polyalkylene oxalates, polyphosphazenes, phosphoryl choline, choline, poly(aspirin), polymers and copolymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one of the aforementioned polymers.

As used herein, the terms polyglycolide, poly(D,L-lactide), poly(L-lactide), poly(D,L-lactide-co-glycolide), and poly(L-lactide-co-glycolide) can be used interchangeably with the terms poly(glycolic acid), poly(D,L-lactic acid), poly(L-lactic acid), poly(D,L-lactic acid-co-glycolic acid), or poly(L-lactic acid-co-glycolic acid), respectively.

Biobeneficial Material

In some embodiments, the TMDS device can optionally include a biobeneficial material. The combination can be mixed, blended, or patterned in separate layers. The biobeneficial material described herein can be a polymeric material or non-polymeric material. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly(ether-esters), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, poly isobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Use of the TMDS Device

In accordance with embodiments of the invention, the TMDS device can be used to treat or ameliorate a skin condition or other tissues conditions. Examples of such skin condition include burn wound and other non-healing or infected cutaneous wounds, e.g., chronic diabetic ulcers and necrotizing fasciitis. Examples of non-skin conditions include but are not limited to muscle injury, bone injury, cartilage injury.

EXAMPLES

Embodiments of the present invention are illustrated by the studies described below, which shall not be read to limit the scope of the present invention.

Example 1

In Vivo Studies Using Porcine Models

1. Rationale

Pig and human skin have significant similarities ranging from: 1) skin anatomic structure; 2) skin mechanical properties; and 3) biological mechanism of wound and burn healing. First of all, from an anatomic and physiologic standpoint, pig skin is much more similar to human skin than other mammals[91]. The cornified layer and epidermis of the pig is relatively thick, similar to that of humans. Like humans, pig dermis is composed of two zoned: the well-defined papillary dermis and the dense reticular dermis[92]. From a vascular standpoint, pig skin, like human skin, also contains a superficial dermal papillary plexus as well as a deeper dermal cutaneous plexus[93].

Second, with respect to mechanical properties, pigs and humans are considered fixed skin animals in which substantial connections exists between the skin and the deep fascia[94]. In contrast, most experimental animal models (e.g., rodents, rabbits, dogs, etc.) are considered "loose skin" models due to lack of substantial attachments of the skin to the deep fascia[95]. Most loose skin animals have a panniculus carnosus muscle (not present in humans) that is firmly attached to the reticular dermis, but not the deep muscular fascia. Meanwhile, although pigs do have a panniculus carnosus muscle, the muscle is attached not only to the reticular dermis but is also attached through hypodermal fiber networks to the deep muscular fascia[94]. From a wound healing standpoint, loose skin animals tend to heal more by wound contraction and are less reflective of human wound healing, while fixed skin animals (e.g., pig) heal primarily by granulation tissue formation and wound reepithelialization and are more reflective of human wound healing[95].

Third, for burn wound healing, there are several, well defined, histopathological models of porcine burn injury[1,13,93,96] as well as several general models of porcine burn injury[71,97-100]. Sullivan et al., reviewed over 180 articles looking at different animal wound models and found a 78% concordance between results in humans vs. pig, versus only 53% in humans vs. small mammals[91]. Taken together, pig burn models much more closely simulate human burn healing than rodent models.

In the studies described herein, all the aforementioned properties of pig skin are critical to the design and implementation of TDD devices that would work on human skin. For example, the similarities between human and pig skin mechanical properties are critical for achieving satisfactory TDD material composition and design specifications that can be applied to human skin penetration. In addition, the presence of superficial and deep dermis vascular plexus in pig skin that are anatomically similar to human skin will facilitate fabrication of TDD devices that minimize vascular trauma and bleeding.

An example of porcine models for cutaneous wound healing is shown in FIG. 1: A. Porcine full-thickness primary intention healing model. Sutured 1.5 cm wound immediately after surgery. B. Hematoxylin & Eosin (H&E) stained sections at 4 weeks (green arrows demarcate wound site), 40×. C.

Picrosirius red (PSR) collagen staining (green arrows demarcate wound site), 40×. D. Confocal image of dermal scar and corresponding unwounded dermis (D'), 630×. E. Porcine full-thickness secondary intention healing model. 5-mm punch biopsies immediately after surgery, covered in adherent wound dressing. F. H&E at 4 weeks (yellow arrows demarcate wound site), 40×. G. PSR collagen staining (yellow arrows demarcate wound site), 40×. H. Confocal image of dermal scar and corresponding unwounded dermis (H'), 630×.

2. Studies of TDD-Like Devices in Porcine Skin

Figure 2:
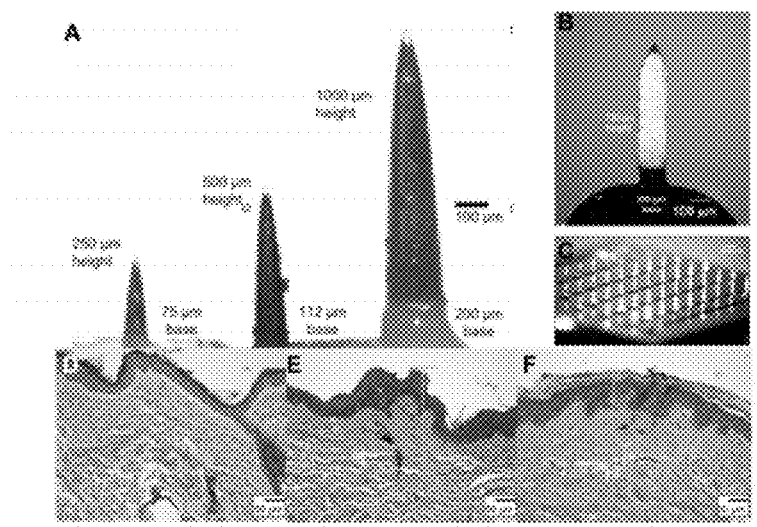
FIG. 2 shows H&E stained sections of microneedle treated rodent and pig skin. A. Dermatologic microneedles fabricated from stainless steel. A. Dermatologic microneedles fabricated from stainless steel. Note various needle dimensions and structures. B. Pharmaceutical microneedles from Gill et al.[2], showing sample needle dimension and shape. C. Note the microneedle array. D. 1000 µm microneedles on rat skin showing ink penetration (green arrows) up to ~340 µm into the dermis. E. 500 µm microneedles on pig skin showing ink at ~244 µm (blue line). F. 250 µm microneedles on pig skin showing ink at ~160 µm (blue line).

The concept of TDD device fabrication evolved from our work with microneedles. FIG. 2 demonstrates delivery of India ink dye to rat and porcine skin using non-dissolvable stainless steel microneedles of various dimensions. FIG. 2 shows H&E stained sections of microneedle treated rodent and pig skin. A. Dermatologic microneedles fabricated from stainless steel. Note various needle dimensions and structures. B. Pharmaceutical microneedles from Gill et al.[2], showing sample needle dimension and shape. C. Note the microneedle array. D. 1000 μm microneedles on rat skin showing ink penetration (green arrows) up to ~340 μm into the dermis. E. 500 μm microneedles on pig skin showing ink at ~244 μm (blue line). F. 250 μm microneedles on pig skin showing ink at ~160 μm (blue line).

From a TDD fabrication standpoint, the force required for initial eschar penetration and the penetration depth will depend on the individual TDD characteristics as well as the elasticity and tension (i.e., mechanical properties) of the skin (reviewed in[89]). For example, using small scale TDDs such as microneedles, Lee et al. reported penetration depths of only 150-200 μm using microneedles with 600 μm length, 300 μm base, and 300 μm interspace[86]. This was attributed to inherent skin viscoelasticity causing skin surface deformation during microneedle application[86]. We have also found this to be the case when we compared penetration of microneedles in rat skin vs. pig skin.

Using 1000 μm length needles, we found penetration depth of 340 μm in rat skin, and minimal penetration when using 250 μm length needles (FIG. 2). In contrast, using less force on pig skin we could achieve average penetration depths of ~160 μm using 250 μm length needles and ~244 μm depths using 500 μm length needles. This is due to the "loose skin" nature of rodent models that is distinct from non-loose skin pig models that closely approximate human skin. These studies underscore that the inherent skin viscoelasticity differences between pig skin and rodent skin and the rationale for TDD design and testing in porcine models. More importantly, these studies demonstrate the ability of micro-sized TDD-like devices to deliver substances deep into the dermis. Drug delivery depth can be regulated by the length of the TDD. Drug delivery amount can be regulated by the total volume/absolute dimensions of the TDD. Drug delivery duration can be regulated by dissolution/degradation profiles of materials chosen for TDD and SDR fabrication. Overall, the use of rapidly dissolving TDD-SDR devices should increase the total does, uniformity, and sustainability of subeschar tissue drug delivery.

3. Dissolvable TDD Devices

Figure 3:
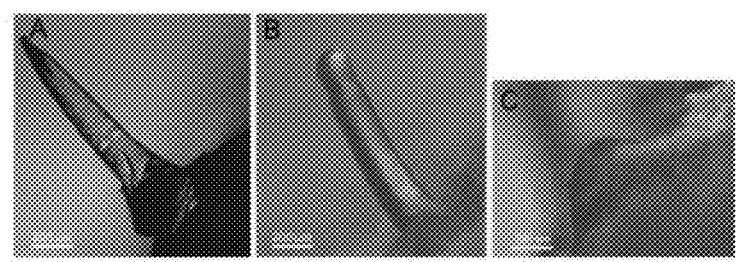
FIG. 3 shows an embodiment of dissolving TDD device fabricated with 6% CMC with 0.5% Polyethylene Glycol (PEG) coating. A. The resultant needles shown capture good details of the PDMS molds with no dissolution yet. The needle length is ~1 mm and the base diameter ~0.25 mm. First, 50 µl PEG is used to coat the plasma-etched (1 min.) PDMS mold and dried in the oven at 40° C. for 45 minutes. Then 100 µl 6% CMC solution is pipetted to the coated mold and dried in the 40° C. oven for 4 hours. A) Represents no dissolution. B. Represents 20% dissolution after ~2 minutes hydration. C. Represents >75% dissolution after ~5 minutes hydration.

Carboxymethyl cellulose (CMC), a readily soluble and commonly used pharmaceutical excipient that is on the FDA's GRAS (generally recognized as safe) list has been used to make microneedles[86]. However, CMC bonds strongly with poly(dimethylsiloxane) (PDMS) molds, which makes de-molding challenging. Previous studies have used a ~27 wt % CMC concentration about. High concentration provides the CMC needles with good mechanical properties; however, the resultant high viscosity increases the difficulties for CMC solution to fill in the PDMS molds. We have developed a vacuum assisted filling protocol to effectively flow viscous CMC solutions into microneedle PDMS reservoirs that have been pre-coated with PEG in order to facilitate de-molding. FIG. 3 shows an embodiment of fabrication of dissolving TDD devices made with CMC. FIG. 3 shows dissolving TDD device fabricated with 6% CMC with 0.5% Polyethylene Glycol (PEG) coating. CMC and PEG powder is dissolved in DI water separately. A. The resultant needles shown capture good details of the PDMS molds with no dissolution yet. The needle length is ~1 mm and the base diameter ~0.25 mm. First, 50 μl PEG is used to coat the plasma-etched (1 min.) PDMS mold and dried in the oven at 40° C. for 45 minutes. Then 100 μl CMC solution is pipetted to the coated mold and dried in the 40° C. oven for 4 hours. A) Represents no dissolution. B. Represents 20% dissolution after ~2 minutes hydration. C. Represents >75% dissolution after ~5 minutes hydration.

TABLE 3

Characterization of CMC Mechanical Properties

| $Ag^{NANO}$ in CMC | E-Modulus (GPa) | $CaCl_2$ Solution | E-Modulus (GPa) | Hardness | pH | Average E-modulus (GPa) |
|---|---|---|---|---|---|---|
| 0% | 3.8 ± 0.8 | Blank | 3.8 ± 0.8 | 13.2 ± 0.4 | Blank (pH 7) | 3.824 |
| 0.5% | 4.3 ± 1.1 | 0.5% | 4.9 ± 0.5 | 21.9 ± 0.5 | pH 5 | 4.703 |
| 2.0% | 4.4 ± 1.3 | 2.0% | 2.4 ± 0.2 | 13.6 ± 0.2 | pH 4 | 3.199 |
| | | | | | pH 3 | 5.342 |

We also performed studies on how various factors including: 1) $Ag^{NANO}$ addition, 2) charge concentration, and 3) charge interactions affect CMC mechanical properties. Specifically, we have already determined that $Ag^{NANO}$ particles improve the stiffness of CMC (e.g., elastic modulus) (Table 3). To determine if charge screening plays a role in CMC strengthening by $Ag^{NANO}$, different concentrations of counter ionic $CaCl_2$ solutions were added to 24% CMC (Table 3). At 0.5% $CaCl_2$, the elastic modulus increases from 3.8 GPa to 4.9 GPa. When $CaCl_2$ concentration is increased to 2.0%, the elastic modulus drops significantly to 2.4 GPa. This trend was repeated in microhardness indentation (500 gf). These data indicate that CMC can be significantly strengthened by selected charge concentrations. For example, to further explore the effects of charge interactions, the modulus of CMC prepared at pH 3, pH 4, pH5, and pH 7 was determined (Table 3). It is believed that lower pH promotes charge interaction and consequently stronger matrix. Table 3 shows the elastic modulus increase to 5.342 GPa at pH 3 comparing to blank CMC, but the value of the modulus slightly decreases at pH 4. At pH 5, the elastic modulus increases back to 4.7 GPa. These data demonstrate that CMC can be significantly strengthened by a desirable pH solution. Collectively, we have shown the feasibility of fabricating dissolvable TDD devices that have the necessary stiffness to penetrate skin.

4. Studies on Efficacy of Nanosilver Against *S. Aureus*

In the studies described herein, antimicrobial efficacy can be evaluated using a microplate proliferation assay described by Bechert et al.[101]. Traditional test systems such as agar diffusion tests measure the zone of bacterial growth inhibition around an agar-implanted test material[101]. Although it is clear that an inhibitory zone reflects the activity of an antimicrobial agent, the size of the inhibitory zone may relate more to drug diffusion capacity in agar than true antimicrobial efficacy. In addition, the agar diffusion method does not provide sensitive and reproducible detection of antimicrobial activities in a proliferation assay reflecting precise antimicrobial dose/bacterial response relationships[101].

Figure 4:
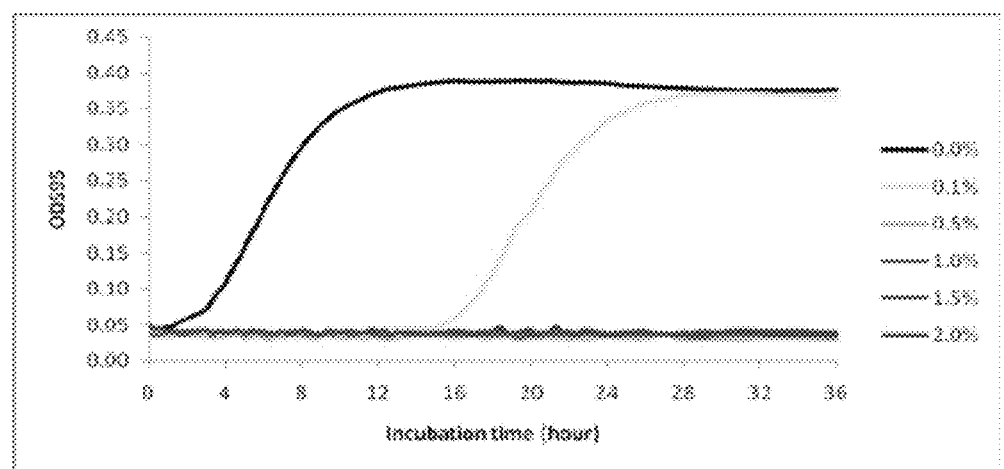
FIG. 4 shows microplate proliferation curve of PLGA-QSI-NS cylinders containing different concentration of QSI-NS.

Poly(lactic-co-glycolic acid) scaffolds coated with 0.1% to 2.0% QSI-Nano Silver (QSI-NS) (QuantumSphere, Inc., Santa Ana, Calif.) were incubated with $10^6$ colony forming units (CFU) of *S. aureus* SA113 in 200 ml of cell suspension. After appropriate dilution, proliferation of the released daughter cells were monitored at a wavelength of 595 nm online by a microplate reader (Infinite F200; Tecan, Switzerland) for the next 36 h to generate a time-proliferation curve for each well of the microplate. Typical time proliferation curves are shown in FIG. 4. Negative bacteriocidal controls (0.0% QSI-Nano Silver) showed uninhibited proliferation. Cylinder containing 0.1% QSI-NS showed inhibited proliferation. Cylinders containing 0.5%, 1.0%, 1.5%, and 2.0% QSI-NS showed no growth, even when the incubation time was extended to 60 h. Similar proliferation curves were demonstrated for *E. coli* (data not shown). These studies validate use of the microplate assay and confirm the antimicrobial efficacy of nanosilver.

5. Studies on Efficacy of Dissolvable Nanosilver TDD Devices

Figure 5:
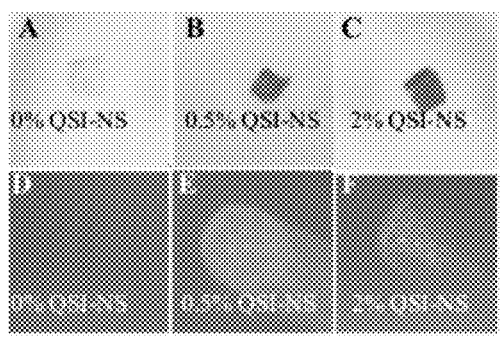
FIG. 5 shows tests results using sheets (5×5 mm) with four individual TDD devices (FIG. 3) per sheet fabricated with 0, 0.5 and 2.0% QSI-NS implanted onto *S. aureus* agar plates. A, B, and C represent time 0 at implant at standard views with the nanosilver appearing dark. D, E, and F represent 24 hrs after implant at inverted views with the nanosilver and inhibition zones appearing light. D shows no bacterial inhibition. E. 0.5%, shows a significant circular area of inhibition. F 2.0% shows a circular area of inhibition, but less than the 0.5%. Note the aggregation.

Dissolvable TDD devices using CMC and QSI-NS were tested for antimicrobial activity. FIG. 5 shows 0.5% QSI-NS creating a significant zone of inhibition on the *S. aureus* coated plate. In the tests in FIG. 5, sheets (5×5 mm) with four individual TDD devices (FIG. 3) per sheet fabricated with 0, 0.5 and 2.0% QSI-NS were implanted onto *S. aureus* agar plates. A, B, and C represent time 0 at implant at standard views with the nanosilver appearing dark. D, E, and F represent 24 hrs after implant at inverted views with the nanosilver and inhibition zones appearing light. D shows no bacterial inhibition. E. 0.5%, shows a significant circular area of inhibition. F 2.0% shows a circular area of inhibition, but less than the 0.5%. Note the aggregation. The nanosilver aggregation at the high 2% QSI-NS concentration creating a smaller zone was not unexpected. Fabrication of sustained delivery/release carriers (SDR) as described in the studies provided above. These studies confirm the antimicrobial efficacy of dissolvable TDD devices.

6. Studies on Polysaccharide Microsphere Preparations for Differential Sustained Time Release Chitosan (CS) is polycationic polymer that forms a crosslinked network with negatively charged ions or molecules such as tripolyphosphate (TPP). TPP is a non-toxic multivalent anionic, has been extensively used as a CS crosslinker. TPP's high charge density ensures a high crosslinking density. Crosslinking density influences important properties of ionically crosslinked CS, such as mechanical strength, swelling, and drug release. Crosslinking density is also influenced by crosslinker concentration as well as CS concentration. CS particles were formed spontaneously from ionic gelation methods by incorporating TPP solution into CS acidic solution. For the association of proteins with CS particles, proteins were incorporated in the TPP solution. Alexa Fluor conjugated bovine serum albumin (BSA) was incorporated into CS particles and the association efficiency of BSA was calculated by measuring the fluorescence with a spectrofluorometer.

Figure 6:
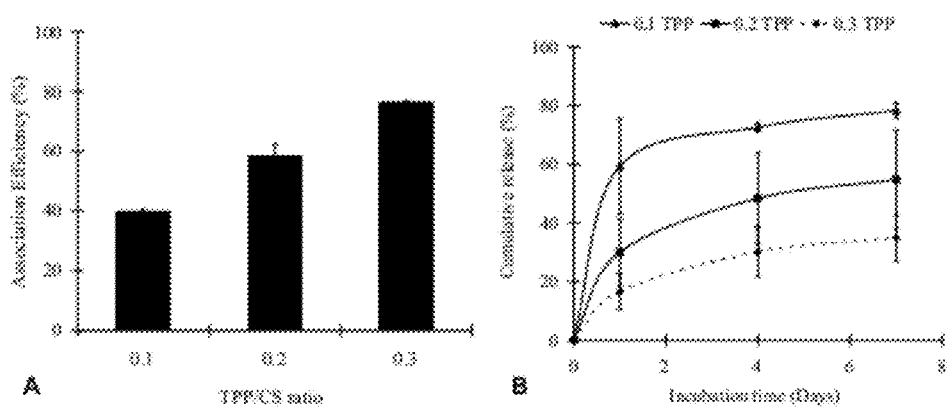
FIG. 6 shows Fabrication of microspheres for sustained drug delivery and retention. A. The association efficiency of BSA as at various concentration of TPP showing increased association efficiency with the higher TPP concentration. B. In vitro release of BSA from the CS particles prepared with a variable amount of TPP (CS/TPP ratio: 0.1, 0.2, 0.3). Slow BSA release was observed with the additional TPP.

FIG. 6 shows fabrication of microspheres for sustained drug delivery and retention. A. The association efficiency of BSA as at various concentration of TPP showing increased association efficiency with the higher TPP concentration. B. In vitro release of BSA from the CS particles prepared with a variable amount of TPP (CS/TPP ratio: 0.1, 0.2, 0.3). Slow BSA release was observed with the additional TPP. The association efficiency of BSA was enhanced from 40% to 76% with increasing CS/TPP ratio (FIG. 6A). BSA-loaded CS particles were incubated in distilled water (DW) at 37° C. and amount of released BSA was determined by measuring the fluorescence of the incubating media. Higher concentrations of TPP in the particle preparation medium led to lower initial bursts of BSA from the particles (FIG. 6B). This study demonstrates successful fabrication of sustained delivery microspheres that will allow increased perieschar/subeschar drug retention (i.e., SDR component of TMDS).

7. Studies Using Pig Burn Model

Figure 7:
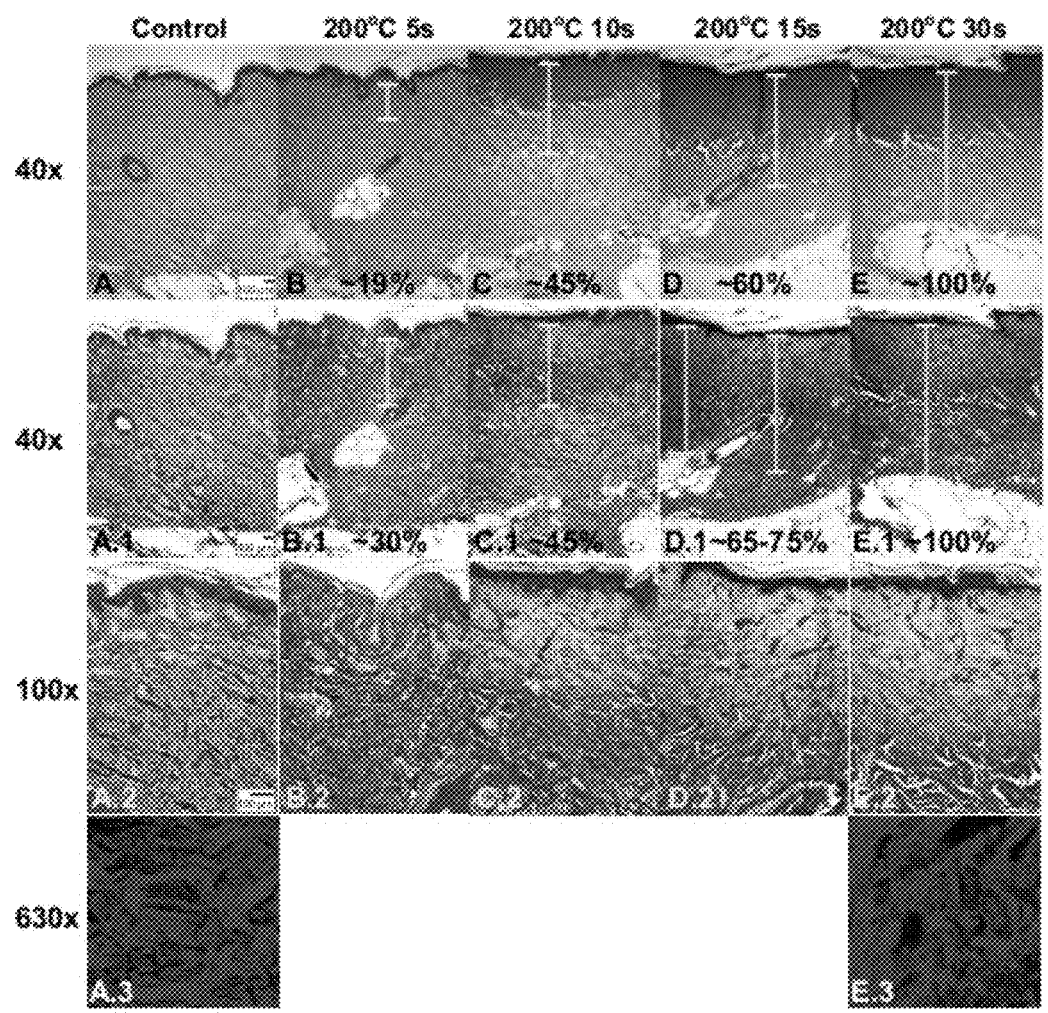
FIG. 7 shows H&E, Masson's trichrome, and confocal sections demonstrating depth of burn injury in pig skin as a function of temperature and heat exposure time. A. H&E of control pig skin at 40×. A.1, A.2. Trichrome of control pig skin at 40× and 100×. Normal, non-denatured collagen stains light blue with defined spacing between collagen fibers. A.3. Confocal of mid dermis collagen at 630×. B, B.1. 200° C. for 5 seconds (s) yielded ~19-30% dermal thickness injury. B.2. Note darker collagen staining and moderate loss of interfiber spacing. C, C.1. 200° C. for 10 s yielded ~45% dermal thickness injury. C.2. Note increased red dermal staining indicative of denatured collagen. D, D.1. 200° C. for 15 s yielded ~60-75% dermal thickness injury. Note level of hair follicle (blue arrow) and apocrine gland (green arrow). D.2. Note further increased red dermal staining indicative of denatured collagen. E, E.1. 200° C. for 30 s yielded ~100% dermal thickness injury. E.2. Note red discoloration indicative of collagen denaturation. E.3. Note altered mid dermal collagen architecture on confocal.

We systematically tested different temperatures (100° C., 200° C., 300° C., and 400° C.) and different exposure times (5, 10, 15, 30, and 60 seconds) on dorsal pig skin. FIG. 7 shows H&E, Masson's trichrome, and confocal sections demonstrating depth of burn injury in pig skin as a function of temperature and heat exposure time. Specimens were fixed immediately after burning. The % dermal collagen injury depth was determined by 1) measuring on H&E the vertical distance between the cutaneous basement membrane and the deepest level of bluish or magenta collagen discoloration from burn injury (yellow lines) as described by Singer et al.[1] or 2) measuring on Masson's trichrome the vertical distance between the cutaneous basement membrane and the deepest level of dark blue collagen discoloration divided by total dermal thickness. A. H&E of control pig skin at 40×. A.1, A.2. Trichrome of control pig skin at 40× and 100×. Normal, non-denatured collagen stains light blue with defined spacing between collagen fibers. A.3. Confocal of mid dermis collagen at 630×. B, B.1. 200° C. for 5 seconds (s) yielded ~19-30% dermal thickness injury. B.2. Note darker collagen staining and moderate loss of interfiber spacing. C, C.1. 200° C. for 10 s yielded ~45% dermal thickness injury. C.2. Note increased red dermal staining indicative of denatured collagen. D, D.1. 200° C. for 15 s yielded ~60-75% dermal thickness injury. Note level of hair follicle (blue arrow) and apocrine gland (green arrow). D.2. Note further increased red dermal staining indicative of denatured collagen. E, E.1. 200° C. for 30 s yielded ~100% dermal thickness injury. E.2. Note red discoloration indicative of collagen denaturation. E.3. Note altered mid dermal collagen architecture on confocal. The surface topology of collagen fibers appear ragged and poorly defined, consistent with protein denaturation.

From these studies we determined that 200° C. followed by short (5 seconds) to long (>30 seconds) exposure times was able to induce the full spectrum of superficial (~19-30%), moderate (~45%), and deep (~60-75%) partial thickness dermal injury as assessed by H&E or Masson's trichrome staining (FIG. 7). An desirable injury depth would be to avoid significant injury to the base of epithelial appendages responsible for wound reepithelialization such as hair follicles and apocrine glands. Of note, pigs possess apocrine glands instead of eccrine sweat glands found in human skin. The apocrine glands are typically adjacent to hair follicles and contain a highly coiled lower part situated at the junction of the lower dermis and the stratum adiposum subcutis[102] (FIG. 7D, green arrow).

From these studies we determined that 200° C. applied for 15 seconds was sufficient to achieve deep partial thickness injury and that times exceeding 15 seconds would create a wound that was unlikely to heal within 3 to 5 weeks. Our demonstration of full thickness burn injury at 200° C. for 30 seconds are consistent with results from Branski et al. who noted full thickness dorsal skin injury after application of a 200° C. heated aluminum bar for 30 seconds in 40-65 kg pigs[99] and Singer et al. who also noted 100% dermal collagen discoloration on H&E (indicative of full thickness injury) after applying a 100° C. heated aluminum bar for 30 seconds to dorsal skin of 20-30 kg pigs[1]. Thus, 30 seconds of heat is enough to induce full thickness injury in younger pigs weighing ~20 kg to older pigs weighing 40-65 kg. The overall weight/age of the pig as well as the burn location are important for experimental consistency. For example, ventral skin thickness was 1.6 mm in the 13-week-old pig which increased to 2 mm in 1 year-old animals. For dorsal sites the increase in skin thickness was from 2 mm to 5 mm over the same time period (reviewed in[103]). To ensure consistency, we have used pigs within a narrow range of age and weight (~20-25 kg). The dorsal dermal thickness in ~20 kg pigs is ~2 mm[102]. These studies demonstrate creation of a porcine model with defined burn injury depths that correlate well on both H&E and Masson's trichrome staining.

Figure 8:
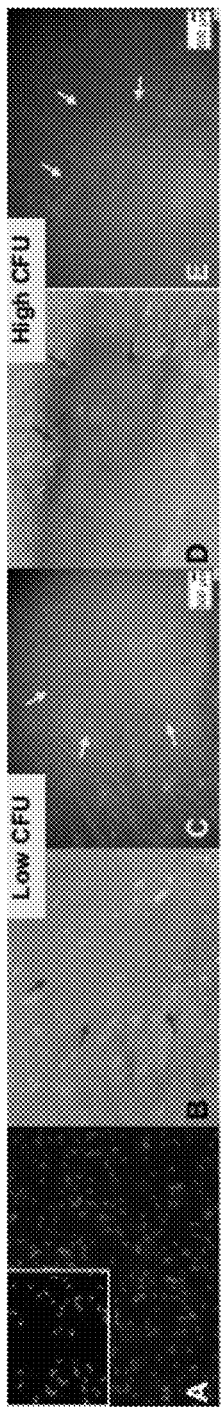
FIG. 8 shows fluorescent E. coli grown in Luria Bertani (LB) plate and in pig skin. A. RFP and GFP (inset) expressing E. coli on LB plate, 1000×. B. To the right of the red arrows is the portion of burn wound inoculated with low CFU RFP-E. coli. not visible to the naked eye. C. Same wound as "B" with fluorescence lighting shows RFP expression. D. To the left of the red arrows is the portion of burn wound inoculated with high CFU RFP-E. coli. visible to the naked eye. E. Same wound as "D" with fluorescence lighting showing significant RFP expression.

8. Studies on Visualizing Fluorescence Labeled Bacteria Application to Burned Pig Skin We have inoculated relatively low (~$10^6$ CFU/ml) and high (~$10^{12}$ CFU/ml) E. coli expressing green fluorescent protein (GFP) or red fluorescent protein (RFP) to burned pig skin and assessed bacteria growth 24 hours later. FIG. 8 shows data for RFP-E. coli. Importantly, the bacteria could be visualized on the burned tissue surface by the naked eye at high CFUs and by applying fluorescence imaging at low CFUs (FIG. 8). In FIG. 8 E. coli was shown to grow in Luria Bertani (LB) plate and in pig skin. A. RFP and GFP (inset) expressing E. coli on LB plate, 1000×. B. To the right of the red arrows is the portion of burn wound inoculated with low CFU RFP-E. coli. not visible to the naked eye. C. Same wound as "B" with fluorescence lighting shows RFP expression. D. To the left of the red arrows is the portion of burn wound inoculated with high CFU RFP-E. coli. visible to the naked eye. E. Same wound as "D" with fluorescence lighting showing significant RFP expression. These studies validate the use of fluorescent bacteria in our pig infection model.

Example 2

Design, Fabrication and In Vitro Studies on TMDS Devices

1. Decreasing Wound Bioburden Through Local Enhancement of Wound Healing

Infection control and wound healing are integrated processes. Healing of contaminated bone or soft tissue defects is in essence, a "race" between infectious organisms that seek to contaminate, colonize, and ultimately infect the tissue and the body's endogenous tissues that seek to grow into and ultimately close the defect. A critical component to winning this race is the concept of wound bioburden, defined as the microbial load placed on wounds by bacterial cells and their chemical products[42]. The degree of manageable wound bioburden will vary depending on the host and the virulence of the infectious organism. For instance, a healthy, 20 year-old male may be able to tolerate a higher bioburden than a 70 year-old male with diabetes, renal failure, and microvascular disease. However, the basic principles of bioburden control remain the same. These consist of either physically removing the bacteria/bacterial products/biofilms (e.g., by surgical debridement, VAC devices, etc.) and killing and/or preventing growth of the bacteria (e.g., antibiotics and antiseptics)[42] through methods with as minimal cellular toxicity as possible as described above.

Besides decreasing bioburden and preventing iatrogenic toxicity, it is also critical to desirably obtain local wound healing by maximization of "pro-healing" endogenous host factors (e.g., nutrition, immune status, metabolic status, vascular supply, etc.) as well as "pro-healing" exogenous host factors (e.g., exogenous growth factors, bioengineered constructs, etc). Gel formulation recombinant human PDGF (rhPDGF)-BB homodimer was approved in December 1997 for adjunct treatment of lower extremity diabetic neuropathic ulcers[67,68] (i.e., becaplermin; Regranex 0.01% Gel, Ortho-McNeil Janssen Pharmaceuticals, Inc.). RhPDGF-BB combined with β-tricalcium phosphate was approved in November 2005 as bone graft material for periodontal procedures[69,70] (GEM 21S-Growth Factor Enhanced Matrix, Osteohealth, Shirley, N.Y.). With respect to pharmacotoxicity, becaplermin has undergone extensive safety testing with up to 3 mg/kg (~214 X over the recommended human dose of 14 µg/kg/day) given subcutaneously or intravenously in mice, rats, and monkey with no significant acute toxicity or any mortality[3,4].

Naturally occurring PDGF from human platelets is a ~30 kDa heterodimer composed of two peptide chains, designated A and B, which share ~60% homology at the amino acid level[71]. Human results with becaplermin have been somewhat inconsistent with some studies demonstrating no significant difference in incidence of complete diabetic foot ulcer healing in becaplermin vs. good ulcer care alone[68] and some studies demonstrating increased incidence of complete healing as well as time to complete healing[72]. Part of the reasons for lack of becaplermin efficacy in chronic wounds may be due to its short half life of 4 hours[3], excessive protease activity in chronic wounds[73], poor penetration[3] and lack of carriers for sustained delivery in its present Regranex 0.01% Gel formulation. Jin et al. implanted scaffolds with and without microspheres for sustained becaplermin release into a subcutaneous rat model[74]. By day 7, scaffolds with sustained becaplermin release demonstrated significantly increased cell migration, tissue ingrowth, and vasculogenesis at lower becaplermin doses[74]. These studies indicate that when penetration and sustained delivery issues are addressed, becaplermin can significantly increase tissue neogenesis and angiogenesis.

Another reason for the differences in perceived efficacy may be in decision to select time to wound closure or complete healing as the clinical endpoint. From a biological standpoint, wound closure of a full thickness defect requires at minimum, epithelial-mesenchymal interactions consisting of granulation tissue formation by mesenchymal cells (e.g., fibroblasts and endothelial cells) at the wound base and reepithelialization by keratinocytes at the wound edge[75,76]. While most mesenchymal cells contain receptors for PDGF, keratinocytes do not[76]. Thus it is entirely possible that becaplermin may significantly increase tissue ingrowth/angiogenesis without necessarily increasing reepithelialization—the final endpoint for complete wound closure. This observation is supported by animal models in which PDGF-BB application significantly increased granulation tissue formation, but did not promote faster reepithelialization in diabetic rodent wounds[77] or full thickness pig burn wounds[71]. Of even more interest, plasmid mediated PDGF-BB expression promoted survival of ischemic myocutaneous flaps in a rabbit model[78]. Collectively, these data indicate that PDGF-BB/becaplermin has consistent effects on promoting tissue ingrowth and angiogenesis, but not reepithelialization—and raise intriguing clinical questions on whether becaplermin can: 1) prevent burn wound progression/conversion; 2) accelerate tissue ingrowth into Integra-DRT; and 3) minimize graft loss in contaminated wounds. Thus, using PDGF-BB/becaplermin to promote local wand angiogenesis/tissue growth while simultaneously controlling wound bioburden/infection and iatrogenic toxicities may significantly accelerate tissue healing.

2. Strategies to Improve Efficacy and Decrease Toxicity of Existing Wound Therapies The outermost skin layer, the stratum corneum (SC), is the principle obstacle to topical drug delivery. When intact, the SC favors the delivery of drugs that are small (<500 Da), lipophilic, and potent[79]. While burn injury clearly compromises SC barrier integrity, pharmacokinetics of burn eschar penetration are not well studied[80,81].

Maximizing residual skin and subcutaneous drug delivery in burn wounds requires consideration of: 1) drug penetration through burn eschar; 2) drug movement from burn eschar to viable, vascularized tissues; 3) drug residence time in vascularized tissues; and 4) drug stability/bioactivity. This is likely made more complicated by potential differences in burn eschar composition as well as formation of pseudoeschar or bacterial biofilms[82,83]. For instance, a partial thickness burn with the blister debrided may present different drug permeabilities than a dry, leathery $3^{rd}$ degree burn. On top of this, what is desirable for drug movement through eschar may not be desirable for drug retention in viable tissues.

Moreover, inherent physicochemical properties of the specific drug or drug-carrier formulation such as molecular size, relative lipophilicity, solubility, and octanol water partition coefficient (log $P_{ow}$), contributions of local unbound drug fraction (drug not bound to tissue proteins), drug bound to plasma proteins, and local blood flow are all critical concepts to skin and subcutaneous drug delivery/retention[84].

Fortunately, many of these multifactorial considerations can be bypassed by an active rather than passive drug delivery approach we have termed, Transcutaneous Multimodal Delivery System. Passive drug delivery involves application of drug to the burn eschar and then relying on the inherent physicochemical properties and diffusion of the drug or drug carrier to achieve the desired outcome. In contrast, the TMDS device utilizes a novel modular drug delivery approach that can separately address and then integrate eschar/viable tissue penetration with sustained drug delivery/drug retention. The penetration component of TMDS involves development of dissolvable Transcutaneous Drug Delivery devices that, depending on design/application mode, can penetrate through different depths of eschar and burn tissue, and deliver different drug dosage gradients (e.g., higher concentrations through TDD portion contacting eschar vs. lower concentrations through TDD portion contacting viable tissues). The Sustained Delivery and Retention component involves developing different carrier systems that take into account drug physicochemical properties and desired tissue release/retention parameters. Besides primary goals of sustained tissue release/retention, a secondary goal is to decrease the total drug dose required to minimize overall drug toxicity (e.g., a smaller dose of mafenide acetate may minimize metabolic acidosis). TDD and SDR components are designed to be individually modified and applied or integrated—depending on wound requirements.

The TDD regime evolved from combining the rationale for subeschar clysis in deep burns[85] with dissolvable microneedle technology for percutaneous drug delivery[86]. Subeschar clysis involves using conventional hypodermic needles to directly inject antimicrobials under the burn eschar[85]. In practice it is rarely used because of difficulty with uniform and sustained drug delivery/retention as well as lack of information on whether large fluid volumes injected under pressure in edematous burn tissues will cause further tissue ischemia and/or drive bacteria further into the wound—as is the case with high pressure lavage in orthopedic injuries[87]. Meanwhile, microporation of the SC using dissolving or non-dissolving microneedles is an exciting technology that involves creation of multiple, micron-sized channels through the SC to the viable epidermis[88-90]. The micron-sized channels made by microneedles are smaller (needle base diameter ~75-200 μm) and shallower than the holes made by hypodermic needles (the smallest hypodermic needle is 31 gauge with a needle diameter of ~305 microns). To avoid causing pain and bleeding, the microneedle lengths are controlled so that they do not reach the pain sensing nerve fibers and blood vessels in the underlying dermis[88]. Microneedles have successfully delivered peptides such as desmopressin (1.4 kDa) and larger proteins such as ovalbumin (45 kDa) in vivo (reviewed in[89]) as well as delivery of microparticles ranging from 1 to 10 μm diameter in vitro[2]. Microneedles, however are only intended to precisely deliver small drug volumes through a small defined area of non-injured skin. In contrast, TDDs are intended to cover large TBSA and are designed to not just penetrate the SC, but to penetrate through bacterial sanctuaries such as biofilm and eschar to reach viable tissue to create a protective antimicrobial zone that is inhospitable to pathogenic microorganisms. Relative to conventional hypodermic needles, the smaller diameter TDDs are fabricated as large array sheets to allow more uniform and controlled therapeutic delivery through smaller diameter devices.

The TMDS device of invention is intended for use as a supplementary wound dressing directly over partial and/or full-thickness burns, donor sites, skin grafts, skin substitutes (e.g., Integra-DRT), acute/subactue/chronic wounds, and wound with exposed bone/tendon. TMDS can be applied under general anesthesia in the operating room or under sedation at the bedside during initial wound debridement. For small TBSA wounds, local anesthetic (e.g, topical lidocaine gel not exceeding 5 mg/kg total dose) can be applied before TMDS application. For TMDS application over skin graft or Integra-DRT, the TDD component should penetrate (depthwise) through the graft or Integra and a portion of the wound bed. The TMDS device of invention can be secured using conventional wound dressing materials such as absorbent gauze rolls, elastic bandages, or wound devices (e.g., VAC). Once applied, dressings or wound devices can be changed as needed without worrying about disrupting the TMDS device of invention. Depending on the SDR component, TMDS can be designed for days to weeks sustained release. For most indications, such as application at initial time of injury or application post skin grafting, 7 day sustained release should be adequate. The penetrating TDD component will dissolve within 30 minutes of contact with body tissues leaving only the SDR component behind (see FIG. 9).

Safety can be demonstrated by findings of no increased local toxicity (e.g., increased local inflammation, immune reaction, or cell death, delayed wound healing, etc.) associated with use of Multimodal Delivery System (MDS) devices. Systemic toxicity (e.g., mafenide associated metabolic acidosis or high serum silver levels) can be addressed by future studies using higher % TBSA burn models. Efficacy can be demonstrated by findings consistent with: minimizing tissue injury/maximizing tissue salvage such as: I) decreased total bacterial numbers in burn wounds; 2) decreased bacteria invasion into perieschar and subeschar tissues; and 3) decreased progression or conversion of burn injury necrosis. Efficacy can also be demonstrated by findings consistent with higher wound closure success such as: 1) increased healing rate/reepithelialization of partial thickness burn wounds; 2) decreased amount of skin graft loss; and 3) faster and/or increased Integra incorporation.

Overall, realization of better infection control and acceleration of wound healing via improved penetration and/or sustained tissue delivery/retention of existing FDA drugs can shorten regulatory development and can improve the current standard of burn care. TMDS can also be applied to other clinical situations where high local concentrations of antimicrobials and/or wound healing promotion factors are desirable (e.g., chronic diabetic foot ulcers, wounds after debridement for necrotizing fasciitis).

3. TMDS Devices

Delivery Efficacy and Toxicity

Figure 9:
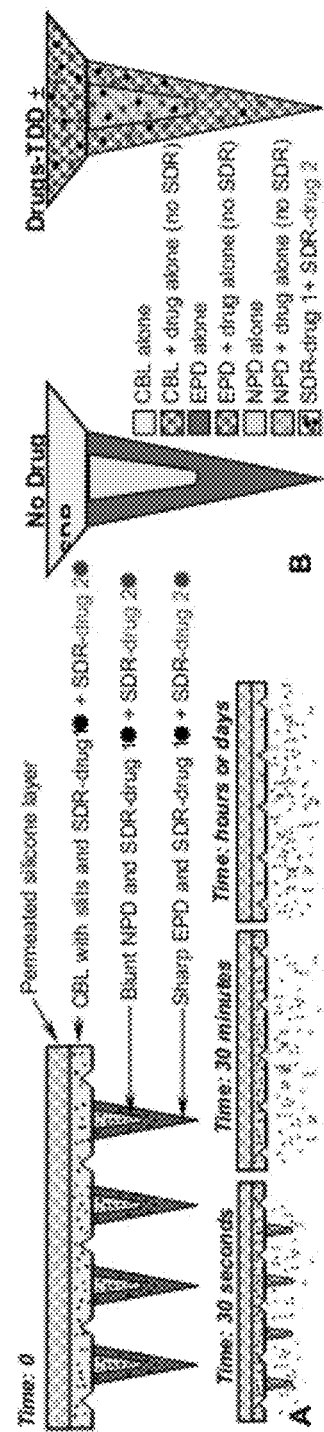
FIG. 9 shows an embodiment of the TMDS device of invention with TDD and SDR components; TDD subelements: silicone layer, CBL, NPD, and EPD. A. At time 0, all TDD subelements are present. By 30 sec, the EPD element is dissolved with release of free-drug as well as SDR-drug. By 30 min, the NPD element is dissolved with release of free as well as SDR-drug. Drug is also released from the CBL element from irrigation through the silicone layer. B. Magnified view of TDD component.

The complex nature of the biological and microbiological environment necessitates a modular TMDS design that is clearly different from previously published microneedles in terms of functionality and complexity. FIG. 9 shows an embodiment of the TMDS device with TDD and SDR components; TDD subelements: silicone layer, CBL, NPD, and EPD. A. At time 0, all TDD subelements are present. By 30 sec, the EPD element is dissolved with release of free-drug as well as SDR-drug. By 30 min, the NPD element is dissolved with release of free as well as SDR-drug. Drug is also released from the CBL element from irrigation through the silicone layer. B. Magnified view of TDD component. Whereas previous microneedles are comprised of single components, an embodiment of the modular TDD design comprises of 4 subelements: 1) an external permeable silicone layer that facilitates drainage of wound exudate; 2) a backing layer, or conformable backing layer (CBL), that conforms over irregular eschar surfaces; 3) blunt non-vessel penetrating device (NPD) that dissolve in ~10-30 min; and 4) sharp eschar penetrating device (EPD) that dissolves rapidly <30 sec (FIG. 9A). Modular SDR elements can be added to the TDD device to create the TMDS. To facilitate uniform material processing TDD systems, microparticulate SDR components will not compositionally exceed 15% by volume. Drugs in SDR will undergo sustained release (release duration depends on SDR/TDD materials and therefore can be control according to a desired release profile). Drugs in TDD components (CBL, NPD, or EPD) without SDR will undergo more acute release (FIG. 9B). Because the drug sizes are significantly smaller than SDR systems (e.g., $Ag^{NANO}$ is 25 nm; MA is a small molecule drug $C_7H_{10}N_2O_2S$), they are not expected to significantly affect TDD processing or physical/mechanical properties as long as they are chemically compatible with the TDD materials. Drug-carrier compatibility can be modulated by controlling surfactant composition and concentration.

To define how SDR element addition may change TDD mechanical properties, all TDD subelements can be tested at 0% and 15% by volume SDR composition. If significant differences in mechanical properties are noted with 15% SDR addition, then smaller amounts of SDR and/or alternative TDD materials can be explored. To more closely approximate in vivo conditions, all test can be performed at normothermic porcine temperatures of 38° C.[93]. To minimize the total number of test animals/test sites needed, initial TMDS devices (each containing multiple TDDs) can have a relatively small total square area, e.g., 1 cm×1 cm or 2.5 cm×2.5 cm. The initial goal for TDD penetration depth is 1 cm.

Design, Fabrication, and Ex Vivo/In Vivo Testing of TDD Systems

1) Studies on Penetration, Conformability, Dissolution, and Diffusion on Cadaveric Pig Tissue a. TDD Design and Fabrication TDD systems disclosed herein are capable of: 1) penetrating different wound surface conditions (e.g, dry, leathery $3^{rd}$ degree burn, moist, $2^{nd}$ degree burn, excised subcutaneous wound bed; and normal skin); 2) conforming to different wound contours (e.g., convex, concave, irregular surfaces); 3) defined dissolution kinetics; and 4) overlapping diffusion zones (i.e., no "cold spots" with no drug delivered). These attributes are interrelated processes that need to be considered together for a desirable TDD design. Specifically, the force required for initial eschar penetration and the penetration depth will depend on the individual TDD shape (e.g., conical vs. cylindrical), TDD geometry (base width/diameter, height/length) inter-TDD spacing, tip sharpness, TDD fabrication material, and the elasticity and tension of the skin (reviewed in[89]), while diffusion zones depends in large part on TDD shape/geometry as well as inter-TDD spacing.

The large surface areas that are typically involved large burns require us to come up with alternative manufacturing strategies that can produce much larger sheets (meters) than previous microneedle sheets made with microfabrication and centrifugal casting (centimeters). The proposed needles are also much longer (~1 cm) than previously reported microneedles (<1 mm), and the processing of longer needles introduce additional materials engineering challenges such as air trapping that much be addressed in order to maximize needle production yield. To address the need for multiple materials in the four TDD components, we have developed an elegant overmolding method to mold additional material (e.g. sharp eschar penetrating device) over previously molded materials (e.g. blunt, non-vessel penetrating device). We have also developed a practical negative pressure system to draw air out of the long needle molds prior to filling the needle molds with the needle material. The addition of negative pressure greatly reduced the frequency of air bubbles at the needle tips, and dramatically increased the yield of intact needles.

b. Studies on Penetration

For TDD to be effective, the device must penetrate through burn eschar to reach bacterial sanctuaries so as to confer a three dimensional antimicrobial zone that is inhospitable to pathogenic microorganisms. Although the eschar can be soft and pliable in some patients, these tissues can be rather tough in others, depending on trauma history and degree of hydration. However, the need for sharp needles to penetrate the outer eschar layers is offset by the need to avoid vessel penetration injuries, particularly in wound beds with high vascularity. To address these diverging demands on penetration, we propose a novel needle design where an initially sharp needle tip would penetrate the outer tissues, dissolves rapidly (<30 sec), and leaves behind a blunted needle tip that in non-vessel penetrating. The sharp eschar penetrating tip (EPT) can be comprised of hard materials that can dissolve rapidly (<30 sec) in moist tissues at ~38° C. This EPT is over-molded onto blunt, non-vessel penetrating devices that dissolve over 10-30 min (FIG. 9A). Application is intended to be a two- or one-step process depending on the degree of underlying tissue vascularity. Specifically, the entire construct is applied as one step in wound beds with minimal vascularity and low chance of vessel penetration injury. In wound beds with high vascularity and chance of vessel penetration injury, the TDD construct is first penetrated ~200-300 µm into eschar using the sharp, rapidly dissolving tip. With dissolution of the sharp tip within 30 sec, the now blunt-tipped TDD construct is then fully applied into tissue.

Our preliminary data found CMC materials suitable for skin penetration (FIG. 3). If even more stiffness is required, another candidate for ETP layer can be hydroxypropyl methylcellulose phthalate (HPMCP), a cellulose in which some of the hydroxyl groups are replaced with methyl ethers, 2-hydroxypropyl ethers, and phthalyl esters. Other alternatives are described above. Several different types of HPMCP are commercially available with molecular weights in the range 20,000-200,000 Da. Typical average values are 80,000-130,000 Da. As with most polymers of this class, HPMCP mechanical properties and film strength increase with increasing molecular weight. HPMCP will rapidly swell, disintegrate, and dissolve at pH>5, making it a popular coating material in pharmaceutical formulations[104]. HPMCP films can be applied to blunt needle surfaces using a dispersion of the micronized HPMCP powder in an aqueous dispersion of a suitable plasticizer such as PEG, diacetin, acetyl monoglyceride to help prevent HPMCP film from cracking as it dries. PEG may be preferred if dissolution time needs to be accelerated. Conversely, monoglycerides of fatty acids such as acetyl monoglyceride may be necessary if dissolution time needs to be increased. The controlling parameters are therefore: HPMCP molecular weight, HPMCP concentration, plasticizer composition, and plasticizer concentration.

To quantitatively measure the ability of TDD to penetrate SC/eschar without bending or breaking, patches (2.5 cm×2.5 cm) of TDD can be secured to a fixture that is attached to an universal mechanical testing machine (Instron 5860, Norwood, Mass.). The Instron machine can be programmed to measure the load required to continuously advance the needles at controlled crosshead speed of 1 mm/sec into normal or burned cadaver pig skin, and record the load as a function of time and penetration distance. Pig skin is chosen for reasons delineated in the description above. After penetration, the patch can be retracted from the pig skin, and needle shape (% intact, % buckled, % bent, % broken, etc.) can be determined. Based on these criteria, a satisfactory TDD material will penetrate pig skin with minimal force and maximum % intact needle after penetration.

The skin studies provide highly practical information on TDD skin penetration ability, but it is possible that the test may not be able to discern between two TDD different materials that exceed the threshold mechanical properties and therefore penetrate with minimal force and maximum % intact needles. To facilitate engineering design, one can uncouple TDD material properties from pig skin properties by measuring the TDD force-displacement when the TDD is advanced at 1 mm/sec against a flat aluminum plate. Based on these criteria, different TDD materials can be discerned by their different load-to-failure. Taken together, the pig skin penetration test and the load-to-failure test provide two different criteria of evaluating TDD penetration.

c. Studies on Conformability

For TDD to be effective, the needles must be able to conform onto irregular skin/eschar surfaces. For instance, a defect edge may require an abrupt 90° turn. One approach is to select a soft backing layer to hold the needles. However, a soft backing layer may not adequately transfer the stresses to the needles during application. For example, if the backing layer is too flimsy (or lacking in strength) the needles may not be aligned properly for efficient penetration. On the other hand if the backing layer is too rigid, then it cannot adapt over irregular tissue surfaces and tight corners. It is therefore desirable to fabricate a flexible, pliable backing layer out of a relative rigid material, and design a two-dimensional grid of slit spaces within the backing layer (FIG. 9A). This combination allows the material stiffness to facilitate stress transfer and needle alignment, while the slits facilitate contour adaptation over irregular surfaces. One can measure the force required to bend the backing layer from 0° to 90° (conform up) and also from 0° to −90° (conform down) at a cantilever set up.

d. Studies on Dissolution

For this test, EPD can be loaded with 1 wt % methylene blue prior to skin penetration. EPD dissolution can be monitored by device insertion into moist cadaveric pig skin at 37° C., removal at 10, 20, and 30 seconds, followed by immediate visual microscopic evaluation of dissolution. The needles can be dissolved in water and the amount of residual methylene blue quantified by UV-vis spectrophotometer. If the entire EPC dissolved within the skin, then only trace amounts of methylene blue would be detectable in the UV-vis. If EPD is not dissolved, then the entire 1 wt % would be detected. Similarly, independent dissolution tests can be conducted for the blunt, non-vessel penetrating devices at 2.5, 5, 7.5, and 10 minutes.

e. Studies on Drug Diffusion

Methylene blue diffusion into moist cadaveric pig skin at 37° C. can be evaluated by histological analysis to screen and eliminate formulations which do not dissolve. Once suitable formulations are identified, direct diffusion measurements of $Ag^{NANO}$, MA, rhPDGF-BB into moist cadaveric pig skin can be determined by analyzing the histological sections under variable pressure, field emission scanning electron microscope (SEM) equipped with Energy-Dispersive X-Ray analyzing system (EDX) with a build in Raman spectrometer. The Ag signal should be easily discernable by EDX, while mafenide and acetates contain Raman active bonds. The combination of Raman and EDX data with spatial and topological information can allow one to determine the extent of drug diffusion. PDGF has also been reportedly detectable by Raman spectroscopy[105], but the possibility exists that native tissue proteins may lower the signal to noise of PDGF-BB in Raman spectroscopy. In that case one can turn to indirect methods such as immunohistochemistry for PDGF, or we can conjugate PDGF with fluorescent labels. A satisfactory TDD design and materials can produce a three dimensional therapeutic drug zone by releasing $Ag^{NANO}$, MA, rhPDGF-BB into surrounding moist skin (i.e., no "cold spots").

2) Studies on Atraumatic/Hemostatic Insertion Parameters and Dissolution on Live, Non-Injured Pig Tissue Because blood and lymphatic flow in live tissues can impact TDD dissolvability and diffusion, the objective is to obtain desirable TDD materials and design specifications with respect to atraumatic, hemostatic insertion and to confirm dissolvability and diffusion zones on perfused, non-injured pig skin. As shown in FIG. 9, the TDD device is intended to puncture through the superficial dermal papillary plexus (which is typically already coagulated from partial thickness burns) and bluntly displace—but not puncture through—the deeper dermal cutaneous plexus (which would be injured, but perhaps not irreversibly, in partial thickness burns). The working hypothesis is that a conical rather than cylindrical TDD design would accomplish the following: 1) increasing TDD diameter with increased TDD penetration may promote local pressure hemostasis if a more superficial dermal vessel is punctured and bleeds and 2) conical design can minimize local tissue toxicity by allowing more drug delivery to non-viable eschar vs. viable subeschar portion of the wound. If bleeding is encountered, TDD parameters such as increasing the base diameter (more pressure effects), increasing the material dissolution time (prolongs pressure effects), additional tip modifications can be performed.

Design, Fabrication, and In Vitro Testing of SDR Systems

1) In Vitro Assessment of TDD-SDR Systems for Nanosilver Delivery

Taking into account the physicochemical properties of $Ag^{NANO}$, the objective is to fabricate SDR systems using FDA approved biocompatible materials with defined degradation profiles that exhibit sustained bactericidal activity over 7-10 days. Hyaluronic acid (HA) is a natural polysaccharide with a well documented history in human safety for arthritic joint therapy, ophthalmic surgery, drug delivery, and regenerative medicine[106]. The availability of recombinant HA, combined with its short degradation time of ~7 days makes it the ideal starting material for SDR fabrication. In the studies described herein, one can modify HA by conjugating adipic acid dihydrazide (ADH) onto the carboxyl group of HA[107] in order to prolong degradation release duration to 7 days. Briefly, SDR can be made of HA microspheres by preparing by a water-in-oil emulsion by homogenizing an HA (~2,000 kD) solution with ADH solution with mineral oil. The drugs of interest are then added to the emulsion, followed by crosslinking with simple carbodiimide (EDCI) chemistry. After phase separation, multiple rinsing and washing, the SDR can be freeze dried until ready for use. The degree of crosslinking can be modulated by changing the concentration of ADH, EDCI treatment time, and acid exposure steps during crosslinking.

Bactericidal activity of $Ag^{NANO}$ released from TDD-SDR systems can be tested using a microplate proliferation (MP) assay system previously described by Bechert et al.[101] and Alt et al.[108]. More traditional in vitro disc diffusion assays do not show clear correlation between bacteriostatic drugs vs. bactericidal drugs[40] In contrast, MP systems are dynamic assays that can readily distinguish and quantitate uninhibited bacterial proliferation, delayed bacterial proliferation, and no proliferation (see FIG. 4 for example of an MP assay).

Antibacterial activity can be tested against the two of the most common organisms present in burn wounds (Table 1), *S. aureus* and *P. aeruginosa*. These bacteria can also be used to create infected porcine burn wound models. To better visualize bacteria colonization/infection and to better identify sites for quantitative biopsies by holding a fluorescence light source over the infect burn wounds—recombinant RFP expressing *S. aureus* can be generated by transforming *S. aureus* RN4220 (*S. aureus*$^{RN4220}$ from NARSA, Focus Technologies, Inc., Herndon, Va.). *S. aureus*$^{RN4220}$ was selected for transformability with DNA from *E. coli*[109] to utilize the *E. coli* plasmid J61031 containing a rfp gene. To achieve desirable expression of RFP in *S. aureus*$^{RN4220}$, a sarA ribosomal binding site[110] can be PCR-cloned upstream of the rfp gene by incorporating the sarA sequence (5'-TAGGGAGAG-GTTTTAAAC-3') (SEQ ID NO:1) into the upstream PCR primer. The cloned rfp gene with the sarA ribosomal binding site can be ligated to the HincII/PstI site of the polylinker region of the *E. coli-S. aureus* shuttle vector pSK236[111]. The pSK236 vector can confer chloramphenicol resistance to *S. aureus*$^{RN4220}$ (also confers Ampicillin resistance to *E. coli*) for selection of transformed bacteria The *S. aureus*$^{RN4220}$ will remain sensitive to gentamicin. *P. aeruginosa* PAO-1 expressing enhanced GFP (EGFP) can be generated if needed by cloning EGFP coding gene egfp from vector pEGFP-N1 (Clontech) and subcloned into pLZZH13 expression vector, based on the broad-host-range vector pBBR1MCS-2 containing the effective promoter of *Ralstonia eutropha* H16 PHB operon. The construct can be selected in *E. coli* Top10, and then conjugated into *P. aeurginosa* PAO-1 employing *E. coli* S17-1.

In the studies described herein, QSI-Nano Silver at 0.1%, 0.5%, 1.0%, 1.5%, and 2.0% in TDD-SDR can be incubated with $10^6$ CFU of *S. aureus* or *P. aeruginosa* in 200 μl of cell suspension in each well of a 96-well microplate at 37° C. In one set of experiments, the cell suspension can be non-diluted pig serum (SeraCare, Milford, Mass.) (to simulate in vivo protein milieu that can impact $Ag^{NANO}$ oxidation and binding activity) and in a selected bacteria media (to simulate massive in vivo bacteria proliferation in compromised host conditions such as devitalized wounds). Tryptic Soy Broth (TSB) can be used as the medium to simulate massive bacteria proliferation. After incubation for 24 hour, 100 μl bacteria suspension can be amplified by adding 100 μl of TSB medium to a new 96-well microplate. Cell proliferation can be monitored at 595 nm online by a microplate reader (Infinite F200; Tecan, Switzerland) for the next 36 h to generate a time-proliferation curve for each well of the microplate. For each concentration of QSI-Nano Silver, at least four wells can be tested separately. In addition, to determine the duration and the degree of residual QSI-Nano Silver bacteriocidal activity, bacteria can be added to the medium repeatedly. Briefly, at day 0, QSI-Nano Silver in TDD-SDR can be incubated with $10^6$ CFU of *S. aureus* or *P. aeruginosa* in 200 μl of cell suspension in each well of a 96-well microplate at 37° C. $10^6$ CFU bacteria in 200 μl medium can be added to the well on Day 3, 6, and 9, repeatedly. 100 μl bacteria suspension can be collected on Day 2, 4, 7, and 10, respectively, for MP assay as described before.

2) In Vitro Assessment of TDD-SDR Systems for Mafenide Acetate (MA) Delivery

Bacteriostatic activity of MA released from TDD-SDR systems can be assayed as described previously for SDR-$Ag^{NANO}$. Since the clinical dose of MA is 5% in solution and 8.5% in cream form, bacteriostatic concentrations tested can be 0.1, 1, 5, and 8.5%. In addition, MA cream (8.5%, BERTEK Pharmaceuticals Inc., Morgantown, W. Va.) inhibited DNA/protein synthesis and partial thickness donor site healing in rabbits[112]. In addition, combined SDR-$Ag^{NANO}$ and SDR-MA can be assayed to determine whether there can be additive, synergistic, or subtractive effects. If additive or synergistic, combined $Ag^{NANO}$ and MA delivery through TDD-SDR systems can be fabricated and used for subsequent in vitro and in vivo studies.

3) In Vitro Improvement and Assessment of TDD-SDR Systems for Becaplermin (rhPDGF-BB) Delivery The ability of TDD-SDR systems to maintain bioactive PDGF release can be assayed by taking defined aliquots of PDGF released from TDD-SDR at days 1, 3, 5, and 7 and testing it for PDGF activity as described by Pierce et al.[113] Briefly, bioactive SDR-PDGF release can be assayed by proliferation of normal rat kidney fibroblast (NRK, clone 49F; ATCC, Rockville, Md.) with half maximal activity at 0.5 ng/ml PDGF as described by Pierce et al.[113]. Carriers for bioactive protein release are well documented[114], and sustainable PDGF release over a period, e.g., 7 days, can be readily achieved.

PDGF dose is recommended not to exceed 14 μg/kg/day for up to 20 weeks, based on the treatment of a 50 kg individual with a 100 $cm^2$ ulcer receiving 7 μg becaplermin/$cm^2$ (i.e., 700 μg/ulcer)[3,4]. If we assume surface area of ~1.8 $m^2$ for an average sized adult male, this translates into a maximum dose per day of 0.039 μg/$cm^2$ of TBSA. If we then assume that the TBSA treated would not exceed 50% and that the dose can be released in a sustained fashion over 7 days, then the maximum PDGF that can be delivered per $cm^2$ is ~0.54 μg over a 7 day period that can be repeated for 20 times.

Alternatively, if the entire 20 week dose is delivered over the 7 days, then a one time dose of 10.8 µg/cm$^2$ over a 7 day period can be given. Based on these calculations of not exceeding the FDA recommended PDGF doses per cm$^2$, one can test 0.5, and 5 µg/cm$^2$.

In Vitro Toxicity Testing of TDD-SDR Components with Ag$^{NANO}$ MA, PDGF/Ag$^{NANO}$, and PDGF/MA To better predict in vivo responses, the objectives are to better define the in vitro therapeutic dose ceiling for TDD-SDR-Ag$^{NANO}$, TDD-SDR-MA, TDD-SDR-PDGF/Ag$^{NANO}$, and TDD-SDR-PDGF/MA with respect to cell toxicity. Our working hypothesis is that proven antimicrobial TDD-SDR-Ag$^{NANO}$ and TDD-SDR-MA doses in the preceding studies will not be cytotoxic to human cells and that addition of PDGF may decrease—or at the very least not contribute to toxicity. PDGF can be tested at 0.5 and 5 µg/ml. The exact doses of TDD-SDR-Ag$^{NANO}$, TDD-SDR-MA±PDGF can be determined by previous study results. Initially, the lowest bacteriostatic or bactericidal drug levels can be tested and then raised accordingly if no evidence of cytotoxicity. For instance, Alt et al. demonstrated that 1.0% Ag$^{NANO}$ with defined particle sizes of 5-50 nm (Bio-Gate AG) in bone cement was toxic to bacteria but not human osteoblast cell line hFOB 1.19 or mouse fibroblasts[115]. This particle size range is in keeping with published reports demonstrating better antimicrobial activity with silver nanoparticles in the ~10 nm vs. ~60 nm range[52]. In addition, there are numerous studies demonstrating no nanosilver toxicity to osteoblast-like cells[116], MC3T3 cells[117], and human embryonic palatal mesenchyme cells[118]. Alt et al. however did not test Ag$^{NANO}$ doses higher than 1%, so part of our objective in the studies here is to test the higher 1.5% and 2% Ag$^{NANO}$ doses for cytotoxicity. If non-cytotoxic, this can expand the therapeutic dose ceiling for Ag$^{NANO}$ therapy in more virulent or established bacterial infections. However, if there is excessive cytotoxicity, then besides varying the actual dose, we can also experiment with different Ag$^{NANO}$ particle size formulations. For MA, in vitro toxicity has been reported for doses as low as 0.1% for fibroblasts[119] and 0.85% for keratinocytes[120]. Although MA is widely used, both in vitro and in vivo assays do suggest that MA may be more toxic to cells such as keratinocytes[121], fibroblasts[119], and lymphocytes[122] than SSD or perhaps other silver based antimicrobials. In addition, MA cream (BERTEK) inhibited DNA/protein synthesis and partial thickness donor site healing in rabbits[112]. However, 5% MA solution is routinely used on patients as post STSG dressing without apparent delays in graft healing[35], thus it is likely that in vitro toxicity may overestimate in vivo toxicity.

Cell lines used for cytotoxicity testing can be normal human fibroblast cell line WI38 (ATCC CCL75), human adult skin keratinocytes cell line HaCaT, human endothelial-like cell line EA.hy 926 (ATCC CRL 2922), and mouse osteoblastic cell line MC3T3-E1 (ATCC). Viable cell density and proliferation can be assayed on days 1, 3, 5, and 7 using the MTT [3-(4,5-dimethylthiazol-2-yl)-2,5-diphenyl tetrazolium bromide] assay (ATCC). All experiments can be performed in triplicate. Functional cell toxicity can be assayed by cell type: 1) for fibroblasts, procollagen production using ELISA (Takara Bio, Otsu, Japan)[123]; 2) for keratinocytes, keratin expression analyzed by indirect immunofluorescence[124]; 3) for endothelial cells, vimentin,[25] and vascular endothelial growth factor (VEGF) expression[126]; and 4) for osteoblast, ALP staining (Sigma)[127]. Cell viability toxicity can be defined as >50% decrease in proliferation or increase in apoptosis. Cell function toxicity can be defined as >50% decrease in assayed synthetic or activity function. Overall, if excessive toxicity is observed at a particular concentration (e.g., 1% for Ag$^{NANO}$, but not at 0.5% for Ag$^{NANO}$), it suggests that the higher concentration causing toxicity may be more appropriate for sustained release testing using the SDR component rather than rapid release using the TDD component, while the lower concentration would be more appropriate for TDD release.

In Vivo Toxicity Testing of TDD-SDR Components with Ag$^{NANO}$ MA, PDGF/Ag$^{NANO}$, and PDGF/MA The primary objective is to determine what are the highest concentrations/total dose of Ag$^{NANO}$, MA, and PDGF that can be released from TDD-SDR without causing in vivo cell toxicity—i.e., to determine the highest "safe" (nontoxic) dose that can be used in vivo. A second agenda is to sequentially determine whether individual or combined TDD and SDR components (i.e., drug free; without Ag$^{NANO}$, MA, or PDGF) will also elicit adverse effects and if there is any correlation between concentrations/doses causing in vitro toxicity with those causing in vivo toxicity. The drug concentrations in SDR and TDD for testing in Table 4) may change depending on findings in the previous studies on bacteriostatic/bactericidal and in vitro cell toxicity. Testing can be on normal, non injured skin rather than burned skin to eliminate variables related to burn wound progression. In vivo effects on dermal vasculature, inflammation, cell proliferation, apoptosis, and necrosis can be assessed by standard assays. Because even high PDGF doses were not associated with significant toxicity in preclinical studies for becaplermin, PDGF alone will not be tested because it is unlikely that isolated PDGF will exhibit significant toxicity. In addition, one can examine the in vivo degradation profile of the SDR component with special emphasis on any evidence of cell toxicity immediately adjacent to SDRs—since that would represent areas with high local drug concentration. Controls will consist of TMDS with no drug, TDD or SDD components only, and normal skin.

To assay for local toxicity from TDD, SDS, and TMDS (combined SDR/TDD) devices, live, non-injured pig skin can be treated with 1 cm$^2$ TMDS devices containing: 1) different SDR-Ag$^{NANO}$, SDR-MA, SDR-PDGF/Ag$^{NANO}$, and SDR-PDGF/MA concentrations and 2) different TDD concentrations of Ag$^{NANO}$, MA, or PDGF as listed in Table 4. Controls can consist of normal untreated skin, TMDS treated skin (no Ag$^{NANO}$, MA, or PDGF), TDD treated skin (no Ag$^{NANO}$, MA, or PDGF; no SDR); and SDR treated skin (no Ag$^{NANO}$, MA, or PDGF; no TDD).

Young female, domestic pigs weighing 20-25 kg can be used for all pig studies. The 1-cm$^2$ TMDS devices can be applied in a two step process to avoid vascular injury following procedures described above. For application of the SDR without TDD, SDR can be suspended in phosphate buffered saline (PBS) and injected using standard appropriately gauged hypodermic needles to allow egress of the SDR microparticles. After application of TMDS devices and listed controls, the application areas can be kept moist by applying sterile water soaked dressings secured using adherent and elastic bandages. Irrigation catheters may also be applied to maintain appropriate dressing moisture. Skin biopsies can be taken using a round 6-8 mm punch biopsy at 12 hrs, 2, 4, 7, 10, and 14 days to assay for significant adverse effects on dermal vasculature, inflammation, cell proliferation, apoptosis, and necrosis.

TABLE 4

| Drug | Drug Concentration** | | % SDR in TDD | Total Dose (mg/ml) | In Vivo Toxicity Testing of TTD-SDR | | | | | |
|---|---|---|---|---|---|---|---|---|---|---|
| | | | | | Time Points for Tissue Collection | | | | | |
| | in SDR | In TDD | | | 12 hr | 2 d | 4 d | 7 d | 10 d | 14 d |
| | | | | | # 1 cm² TMDS sites/Time Point | | | | | |
| Ag$^{NANO}$ | 0.1% | 0.1% | Up to 15% | To Be Determined | 2 | 2 | 2 | 2 | 2 | 2 |
| | 0.5% | 0.5% | | | 2 | 2 | 2 | 2 | 2 | 2 |
| | 1%$^A$ | 1%$^A$ | | | 2 | 2 | 2 | 2 | 2 | 2 |
| MA | 0.1% | 0.1% | | | 2 | 2 | 2 | 2 | 2 | 2 |
| | 1% | 1% | | | 2 | 2 | 2 | 2 | 2 | 2 |
| | 5% | 5% | | | 2 | 2 | 2 | 2 | 2 | 2 |
| | 8.5%$^A$ | 8.5%$^A$ | | | 2 | 2 | 2 | 2 | 2 | 2 |
| 5 µg$^D$ SDR-PDGF/Ag$^{NANO}$ | 0.1% | 0.1% | | | 2 | 2 | 2 | 2 | 2 | 2 |
| | 0.5% | 0.5% | | | 2 | 2 | 2 | 2 | 2 | 2 |
| | 1%$^A$ | 1%$^A$ | | | 2 | 2 | 2 | 2 | 2 | 2 |
| 5 µg$^D$ SDR-PDGF/MA | 0.1% | 0.1% | | | 2 | 2 | 2 | 2 | 2 | 2 |
| | 1% | 1% | | | 2 | 2 | 2 | 2 | 2 | 2 |
| | 5% | 5% | | | 2 | 2 | 2 | 2 | 2 | 2 |
| | 8.5%$^A$ | 8.5%$^A$ | | | 2 | 2 | 2 | 2 | 2 | 2 |
| Control 1 | 0 | 0 | | Not Applicable | 4 | 4 | 4 | 4 | 4 | 4 |
| Control 2 | | 0$^B$ | | | 4 | 4 | 4 | 4 | 4 | 4 |
| Control 3 | 0 | | | | 4 | 4 | 4 | 4 | 4 | 4 |
| Control 4 | Normal skin | | | | 4 | 4 | 4 | 4 | 4 | 4 |
| Total Wounds Collected/Total # TMDS Sites | | | | | 264 wounds from 264 TMDS sites | | | | | |
| Total Number of Animals/# TMDS Site per Animal | | | | | 12 pigs/~22 1-cm² sites per animal | | | | | |

**Drug concentrations for SDR and TDD may change and can be determined according to ordinary skill in the art.
$^A$May test higher doses if no significant toxicity observed.
$^B$No SDR component or drugs
$^C$An identical amount of SDR as in Control 1 can be injected using standard hypodermic needles with phosphate buffered saline (PBS) as a carrier.
$^D$5 µg/ml PDGF has been proposed for these studies. However, 0.5 µg/ml may be used if better minimization of cell toxicity at the 0.5 µg/ml dose. Because PDGF is known to have a short half life of ~4 hrs³, only SDR-PDGF can be used (i.e., no PDGF in TDD)

Standard H&E staining can be performed. Any evidence of injury to the deep dermal cutaneous plexus or other vasculature can be noted. The degree and type of inflammatory cell infiltrate can be assessed as previously described[128]. Cell proliferation can be assessed by 5-bromo-2'-deoxyuridine (BrdU) labeling as previously described[127,129] with some modifications per Garrett et al.[130] BrdU can be injected intravenously into the jugular vein at a dose of 5 mg/kg 2 hours before tissue biopsy. Biopsied tissues can be immersion fixed for 24 h in either 10% neutral buffered formalin, or Carnoy's fixative. BrdU antibodies for staining can be obtained from Sigma-Aldrich (St. Louis, Mo.). For apoptosis evaluation, in situ terminal deoxynucleotidyl transferase-mediated dUTP Nick-End Labeling (TUNEL) method can be applied to non-sequential decalcified serial sections labeled with the Dead-End Colorimetric Apoptosis Detection System (Promega Corp., Madison, Wis.) as previously described[127,129]. Singer et al. previously established that burn wound progression in a rat contact thermal injury model associates with both early apoptosis and delayed necrosis[14]. High-mobility group 1 (HMGB1) is a mobile chromatin protein that leaks from the nucleus to the cytoplasm of necrotic cells to signal that tissue damage has occurred[14]. Overall, the toxicity pattern observed—both temporally and spatially—can be used to refine the different drug concentrations in SDR and TDD and different % SDR in TDD. After initial application of the TMDS device, achievable local concentrations will primarily depend on the rate of drug release and diffusion kinetics for the specific drug. The diffusion kinetics, in turn, can be determined by the drug concentration gradient that is established.

The established concentration gradient will depend upon the: 1) drug concentration in SDR and TDD; 2) drug release rate from SDR and TDD (determined by how fast the SDR and TDD components dissolve); 3) total SDR-drug and free drug amount within each TDD device; and 4) size/shape/spacing of TDDs within the entire TMDS device. Thus, even if total dose per cm³ (volume of tissue) is kept constant among different TMDS devices, the drug concentration in SDR and TDD components can cause significant variability in biologic activity.

However, it is important to point out that the in vitro cells are exposed to uniform drug doses in the studies described herein since everything is in solution. In contrast, cells in vivo can be exposed to different concentration gradients some of which may be toxic. In other words, for a same total dose of drug (expressed as mg/ml), the local toxicities may be quite different. For example, TMDS formulated with 0.1% SDR-MA and 0.1% TDD with 10% total SDR may result in small overall diffusion gradients (from 0.1% MA), but a large number of MA-releasing SDRs, while TMDS formulated with 1% SDR-MA and 1% TDD and 1% total SDR may result in larger diffusion gradients from a small number of MA-releasing SDRs—all of which can have different implications for cell toxicity and antimicrobial activity. For Ag$^{NANO}$ and MA, if no toxicity is observed at the highest SDR and TDD concentrations specified in Table 4, one can increase the concentration further to better define the in vivo therapeutic dose ceilings. If significant toxicity is observed even at the lowest concentration, one can decrease the concentrations in TDD first and then SDR. If toxicity is still observed, one can decrease the SDR in TDD component, provided that total dose still falls within the antibacterial doses delineated above. With respect to PDGF, it is not anticipated to exhibit any toxicity; however, it can be interesting to determine if there is potentially decreased toxicity with PDGF added.

Example 3

Studies to Test TMDS Ability to Prevent Burn Wound Infection and Burn Wound Progression 1. Establishment of an Infected Pig Burn Model The studies are to establish a standardized porcine infected, partial thickness burn model whereby antimicrobial use/non-use can affect clinically relevant endpoints such as burn wound progression and time to wound closure as assessed by quantitative bacteriology, multiparametric histopathology, and wound healing outcomes. Specifically, one can determine if: 1) TMDS devices can be more effective at preventing wound infection and burn wound progression than standard burn dressings such as Acticoat* 7 and 5% MA solution; 2) TMDS containing PDGF have any effect on burn progression; 3) TMDS devices will accelerate time to wound closure; 3) desirable application schedule for TMDS. Variables, such as thermal contact time and bacteria inoculum can be adjusted such that for a given thermal contact time, the non-bacteria inoculated control burn heals within 3 to 5 weeks, but the bacteria inoculated skin burn progresses to full thickness injury. This would indicate that the contact time produced a partial thickness thermal injury that in the absence of significant bacteria, undergoes minimal burn wound progression. In contrast, the progression of the bacteria inoculated skin burn to full thickness injury indicates that for the same given contact time, the degree of bacteria inoculum was enough to overwhelm the cutaneous defense systems to cause significant bacteria invasion and progression of burn injury. A *S. aureus* and/or *P. aeruginosa* model can be used.

For establishing the depth of thermal injury, one can use protocols described by Singer et al.[1] and Renkielska et al.[96] with some modifications. Domestic female pigs can be anesthetized following standard procedures. Standardized partial-thickness burns can be created on the animals' backs and flanks by applying a 2.5 cm by 2.5 cm by 7.5 cm, 150-gram aluminum bar (Small Part Inc., Miami Lakes, Fla.) preheated in an oven to 200° C.[1]. The bar can be aligned perpendicular to the skin's surface and applied for a period of 5, 10, or 15 seconds (Table 5). Based on our Preliminary Studies (FIG. 7), these contact times would be expected to create a partial thickness injury. A thermocoupled thermometer (Digi-Sense, model no. 8528-20, Cole Palmer Instrument Company, Chicago, Ill.) can be connected to the aluminum bar to measure mean temperature drop during wounding and to calculate energy transfer (#cal/cm$^2$) as described by Breuing et al.[131]. After wounding, a 2×2 cm thin gauze or other temporary bacterial carrier can be placed on the wound and 1.2 ml *S. aureus* bacteria at $10^8$, $10^9$, and $10^{10}$ CFU/ml pipeted onto the carrier. The entire wound can be covered with clear adherent dressing. After 24 hours, the wounds can be irrigated and left open.

TABLE 5

Establishing Infected Partial Thickness Burn Progression Model

| Temperature | Contact Time | # Bacteria (CFU/ml) | Bacteria Exposue Time | \multicolumn{7}{c}{Time Points for Tissue Collection} |||||||
|---|---|---|---|---|---|---|---|---|---|---|
| | | | | 1 d | 2 d | 3 d | 4 d | 7 d | 14 d | 21 d |
| 200° C. | 5 seconds | none | 24 hrs | 4 | 4 | 4 | 4 | 4 | 4 | 4 |
| | | $10^8$ | | 4 | 4 | 4 | 4 | 4 | 4 | 4 |
| | | $10^9$ | | 4 | 4 | 4 | 4 | 4 | 4 | 4 |
| | | $10^{10}$ | | 4 | 4 | 4 | 4 | 4 | 4 | 4 |
| | 10 seconds | none | | 4 | 4 | 4 | 4 | 4 | 4 | 4 |
| | | $10^8$ | | 4 | 4 | 4 | 4 | 4 | 4 | 4 |
| | | $10^9$ | | 4 | 4 | 4 | 4 | 4 | 4 | 4 |
| | | $10^{10}$ | | 4 | 4 | 4 | 4 | 4 | 4 | 4 |
| | 15 seconds | none | | 4 | 4 | 4 | 4 | 4 | 4 | 4 |
| | | $10^8$ | | 4 | 4 | 4 | 4 | 4 | 4 | 4 |
| | | $10^9$ | | 4 | 4 | 4 | 4 | 4 | 4 | 4 |
| | | $10^{10}$ | | 4 | 4 | 4 | 4 | 4 | 4 | 4 |
| Total Wounds Collected/Total # Burn Site | | | | \multicolumn{7}{l}{336 8-mm biopsies collected from 168 2.5 cm$^2$ burn sites} |||||||
| Total Number of Animals/# Burn Site/Animal | | | | \multicolumn{7}{l}{14 pigs/12 2.5-cm$^2$ burn site/animal} |||||||

Once temperature, contact time, bacteria inoculum, and exposure time are defined for *S. aureus*, *P. aeruginosa* can also be used and then refined as needed. If testing *P. aeruginosa*, then another 2-3 pigs are needed.

Specific parameters analyzed can be: 1) degree of wound reepithelialization; 2) bacterial count/gm tissue; 3) ocular micrometer measurements of bacteria invasion depth; and 4) ocular micrometer measurements of thermal injury depth with respect to collagen, endothelial cells, hair follicles, and mesenchymal cells. Quantitative bacteria counts (#CFU/gram tissue) can be as described by Breuing et al.[132] Briefly, samples can be surface decontaminated, weighed, homogenized in 1 ml saline. The homogenate can be serially diluted and aliquots plated for colony counts. Ocular micrometer measurements can be performed as described by Singer et al.[1] Wound reepithelialization can be assessed by taking pictures and wound tracings prior to biopsy. Two 8-mm wound biopsies can be obtained from each 2.5 cm×2.5 cm burn site on days 1, 2, 3, 4, 7, 14, and 21. A fluorescence lamp to identify high fluorescence areas can be used to identify representative (high bacteria #) biopsy sites. Each 8-mm specimen can be bisected and half used for histopathology and half for quantitative bacteria assessment.

Overall, we expect to observe increased thermal contact time and/or increased bacterial inoculum correlate with increased tissue injury and progression of necrosis. If insufficient infection/progression is seen with 24 hour application of bacteria, one can sequentially increase the days of bacteria application up to, e.g., 7 days. If still insufficient, one can increase the depth of burn injury or further increase the bacterial numbers. The depth of bacteria invasion into the wound can be carefully measured at each time point.

TABLE 6

| Ability of TMDS to Prevent Wound Infection/Progression | | | | | | | | | | | | | | |
|---|---|---|---|---|---|---|---|---|---|---|---|---|---|---|
| Dressing Type | Dressing Content | | # Times Dressings Applied | | # 8 mm Tissue Biopsy Wounds per Time Point | | | | | | | | | |
| | | | TMDS | Stand. | 0 | 1d | 2d | 3d | 4d | 7d | 10d | 14d | 21d | 28d |
| TMDS | Ag-MMO | -- | 4x | -- | 6* | 6 | 6 | 6 | 6 | 6* | 6 | 6* | 6* | 6 |
| | | -- | 3x | 1x | 6* | 6 | 6 | 6 | 6 | 6* | 6 | 6* | 6** | 6 |
| | | -- | 2x | 2x | 6* | 6 | 6 | 6 | 6 | 6* | 6 | 6** | 6** | 6 |
| | | -- | 1x | 3x | 6* | 6 | 6 | 6 | 6 | 6** | 6 | 6** | 6** | 6 |
| | | PDGF | 1x | 3x | 6* | 6 | 6 | 6 | 6 | 6** | 6 | 6** | 6** | 6 |
| | MA | -- | 4x | -- | 6* | 6 | 6 | 6 | 6 | 6* | 6 | 6* | 6* | 6 |
| | | -- | 3x | 1x | 6* | 6 | 6 | 6 | 6 | 6* | 6 | 6* | 6** | 6 |
| | | -- | 2x | 2x | 6* | 6 | 6 | 6 | 6 | 6* | 6 | 6** | 6** | 6 |
| | | -- | 1x | 3x | 6* | 6 | 6 | 6 | 6 | 6** | 6 | 6** | 6** | 6 |
| | | PDGF | 1x | 3x | 6* | 6 | 6 | 6 | 6 | 6** | 6 | 6** | 6** | 6 |
| TMDS Control (drug free with moist dressing) | | | | | 6 | 6 | 6 | 6 | 6 | 6 | | | | |
| Standard (Stand.) | Acticoat | | -- | 4x | 6* | 6 | 6 | 6 | 6 | 6* | 6 | 6* | 6* | 6 |
| | 5% MA | | -- | 2x daily | 6 | 6 | 6 | 6 | 6 | 6 | 6 | 6 | 6 | 6 |
| Control | | | | | 6 | 6 | 6 | 6 | 6 | 6 | | | | |
| Total Wounds Collected / Total # Burn Site | | | | | 792 8-mm biopsies collected from 396 2.5 cm² burn sites | | | | | | | | | |
| Total Number of Animals / # Burn Site per Animal | | | | | 33 pigs / 12 2.5-cm² burn site per animal | | | | | | | | | |

*indicates same dressing reapplied
**indicates TMDS dressing replaced with conventional dressings of eiter Acticoat (gray color boxes) or 5% MA solution (blue color boxes).
Once a desirable application frequency for TMDS is defined with respect to S. aureus infections, a similar application schedule cab be used for P. aeruginosa infection, and then refined as needed depending on observable efficacy. If P. aeruginosa models are performed, then another 10-15 pigs are needed.

This is to ensure that sufficiently depth penetrating TMDS devices are fabricated (i.e., the depth of TMDS penetration should exceed the depth of bacteria tissue invasion). Following establishment of a S. aureus model, a P. aeruginosa model can be established. S. aureus was chosen first because it is one of the most common causes of burn related death[132].

1. Examination of TMDS Device Infection Prevention Efficacy

The ability of TMDS devices to prevent wound infection and burn wound progression can be tested using the infected pig model. Compositionally different TMDS devices can be applied as shown in Table 6. These TMDS devices will measure at least 2.5 cm×2.5 cm so as to cover the entire burn wound. S. aureus can be co-applied at a defined CFU/ml that is sufficient to mediate burn wound infection and progression. The efficacy of TMDS devices can be tested against standard burn dressings Acticoat* 7 (a nanocrystalline silver dressing that can be reapplied every 7 days; Smith&Nephew, Hull, UK) and 5% MA solution (BERTEK). All wound dressings/devices can be kept moist in the following fashion: an 8-ply gauze dressing and an irrigation catheter can be secured to each burn wound using Tegaderm. The TMDS and Acticoat* 7 can be kept moist in an occlusive dressing and irrigated 2×/day with sterile water. The 5% MA solution dressing can be kept moist by 5% MA irrigation 2×/day. Controls can consist of infected wounds treated with drug free TMDS and wounds with no treatment except moist dressings. The TMDS controls can assess whether TMDS application can increase bacteria penetration to deeper tissues. Control animals can be sacrificed at 7 days; all other groups can be followed until 28 days—or time to complete wound reepithelialization if sooner. All animals will undergo weekly dressing changes. Animals with TMDS or Acticoat* 7 will undergo reapplication every 7 days. To minimize prolonged delivery toxicities and to determine a desirable TMDS device therapy duration, TMDS can be discontinued at various time points and conventional therapy instituted. The less hyperosmolar 5% MA solution demonstrates less side effects than the previously used 10% cream (current MA cream formulation is 8.5%) with respect to pain on application and neoeschar formation[37]. In addition, Harrison et al. has demonstrated that the 5% MA solution exhibited increased skin absorption compared to the 10% cream[133], while Murphy et al. demonstrated more rapid bacteria control assessed by quantitative wound biopsies using 5% MA solution vs. 10% MA cream in a rat burn model[37].

The efficacy of TMDS devices vs. standard dressing can be assessed by the parameters listed previously (e.g., wound reepithelialization, bacterial count/gm tissue, ocular micrometer measurements of bacteria invasion depth and tissue injury depth). Findings consistent with minimizing tissue injury/maximizing tissue salvage such as: 1) decreased total bacterial numbers in burn wounds; 2) decreased bacteria invasion into perieschar and subeschar tissues; and 3)

decreased progression or conversion of burn injury necrosis, as well as findings consistent with higher wound closure success such as rate/reepithelialization of partial thickness burn wounds can be taken as evidence of increased TMDS efficacy. If increased cell injury is observed upon TMDS application, then standard histopathology assays as described above can also be performed. Overall, PDGF is not expected to have a significant effect on reepithelialization, but it can be interesting too determine if PDGF can modulate the initial amount of burn progression injury.

Example 3

Studies to Test TMDS Ability to Treat Established Burn Wound Infection and Promote Tissue Growth The ability of TMDS devices to treat established wound infection and bacteria invasion can be tested using the infected pig model. Specific objectives are to determine if: 1) well established, full thickness infections can be effectively controlled using TMDS (group undergoing no excision); 2) TMDS pretreatment can significantly decrease bacterial numbers in the eschar and the post-excision (pre-grafting) wound bed; 3) TMDS can improve STSG or Integra-DRT Integra measuring ~3 cm×3 cm can be applied. The STSG can be harvested from the ventral skin using a Padgett Model S dermatome (Integra LifeSciences) set at 0.012 inches. After STSG or Integra application, either the TMDS device+sterile water soaked gauze, Acticoat* 7+sterile water soaked gauze, or 5% MA solution soaked gauze can be applied along with a irrigation catheter. A tie over bolster dressing or stapled dressings can be applied to secure the grafts. The grafts can be irrigated 2×/day. At 7 days after surgery, the grafts can be examined for evidence of adherence and tissue ingrowth. The total area of graft take can be documented by planimetric wound healing assessments, wound healing scores and histology as described by Branski et al[99]. A fluorescent lamp can be shined to see if there is any evidence of the original infecting bacteria. Single 8-mm biopsies can be taken from each graft site every 7 days. To compare side by side STSG take rates when grafting over the Integra sites treated or not treated with PDGF, both Integra sites will undergo grafting at the same time (~2 weeks after Integra placement). If there is significantly more tissue ingrowth in the PDGF treated samples before the 2 post operative weeks after Integra placement, then

TABLE 7

Ability of TMDS to Treat Established Burn Infection
Time Line

| Day 0 Burn + Bacteria | Days 1-4 Establish Infection | Days 5-8 Topical Therapy | | Day 9 Surgical Excision Biopsy (E + WB)[A] | | Day 16 Assess Grafts/Biopsy | Day 23 Assess Grafts/Biopsy | Day 30 Assess Grafts/Biopsy |
|---|---|---|---|---|---|---|---|---|
| All Animals | All Animals | TMDS | Ag[NANO] | STSG | 8 * | Same animal | | |
| | | | | Integra | 8 * | Same animal | | |
| | | | | No excision | 4 * | Same animal | | |
| | | | Ag/PDGF | Integra | 8 * | Same animal | | |
| | | | MA | STSG | 8 * | Same animal | | |
| | | | | Integra | 8 * | Same animal | | |
| | | | | No excision | 4 * | Same animal | | |
| | | | MA/PDGF | Integra | 8 * | Same animal | | |
| | | Standard | Acticoat | STSG | 8 * | Same animal | | |
| | | | | Integra | 8 * | Same animal | | |
| | | | | No excision | 4 * | Same animal | | |
| | | | 5% MA | STSG | 8 ** | Same animal | | |
| | | | | Integra | 8 ** | Same animal | | |
| | | | | No excision | 4 ** | Same animal | | |
| Total Wounds Collected/Total # Burn Site | | | | | | 96 8-mm biopsies collected from 96 2.5 cm² burn sites | | |
| Total Number of Animals/# Burn Site per Animal | | | | | | 8 pigs/12 2.5-cm² burn site per animal | | |

* Indicates same dressing reapplied every 7 days as needed.
** Indicates same dressing reapplied 2×/day as needed.
[A] Quantitative biopsies of eschar "E" and post excision wound bed "WB" can be performed. If *P. aeruginosa* models are performed, then another 8 pigs are needed.

"take" by reducing graft infection; 4) TMDS containing PDGF can accelerate Integra incorporation; and 5) TMDS can improve Integra-DRT graft take to allow earlier grafting. The treatment groups are shown in Table 7. Pigs can be anesthetized and infected burn wounds created as described above. There can be a suitable waiting period to allow for development of a full-thickness invasive infection. The exact time frame of pathologic invasion depth can be defined by results of Example 2; an estimated time frame of 4 days is in placed in the table for illustrative purposes. TMDS devices of suitable penetration depths can be applied (i.e., exceeds depth of bacteria tissue invasion documented in Example 2. After ~4 days of TMDS application, the animals will undergo excision and grafting of their burn wounds. One control group can be treated with TMDS containing Ag[NANO] or MA and will not undergo excision.

Burn wound excision technique is used following standard procedures. After hemostasis, a meshed STSG or meshed both PDGF and non-PDGF treated Integra sites can be grafted sooner. STSG can be performed as described.

REFERENCES

1. Singer, A. J., Berruti, L., Thode, H. C., Jr. & McClain, S. A. Standardized burn model using a multiparametric histologic analysis of burn depth. *Acad Emerg Med* 7, 1-6 (2000).
2. Gill, H. S. & Prausnitz, M. R. Coated microneedles for transdermal delivery. *J Control Release* 117, 227-237 (2007).
3. Regranex. FDA, in http://www.fda.gov/cder/biologics/products/becaomj121697.htm (1997).
4. European Medicines Agency—Regranex. (2003).
5. Church, D., Elsayed, S., Reid, O., Winston, B. & Lindsay, R. Burn wound infections. *Clin Microbiol Rev* 19, 403-434 (2006).

6. Chapter 02 Functions of Skin, in *Principles of Pediatric Dermatology*.
7. Barret, J. P. Initial management and resuscitation, in *Principles and Practice of Burn Surgery* (eds. Herndon, D. N. & Barret-Nerin, J. P.) pp. 1-32 (Marcel Dekker, New York, 2005).
8. Polavarapu, N., Ogilvie, M. P. & Panthaki, Z. J. Microbiology of burn wound infections. *J Craniofac Surg* 19, 899-902 (2008).
9. Kao, C. C. & Garner, W. L. Acute burns. *Plast Reconstr Surg* 105, 2482-2492; quiz 2493; discussion 2494 (2000).
10. Patel, P. P., Vasquez, S. A., Granick, M. S. & Rhee, S. T. Topical antimicrobials in pediatric burn wound management. *J Craniofac Surg* 19, 913-922 (2008).
11. D'Avignon, L. C., Saffle, J. R., Chung, K. K. & Cancio, L. C. Prevention and management of infections associated with burns in the combat casualty. *J Trauma* 64, S277-286 (2008).
12. Cioffi, W. G., Rue III, L. W., Buescher, T. M. & Pruitt Jr., B. A. The management of burn injury, in *Conventional Warfare: Ballistic, Blast, and Burn Injuries* (ed. Zajtchuk, R.F.B.a.R.) 349-377 (US Army Medical Department, Office of The Surgeon General, Washington, D.C. - - - ).
13. Nanney, L. B., Wenczak, B. A. & Lynch, J. B. Progressive burn injury documented with vimentin immunostaining. *J Burn Care Rehabil* 17, 191-198 (1996).
14. Singer, A. J., McClain, S. A., Taira, B. R., Guerriero, J. L. & Zong, W. Apoptosis and necrosis in the ischemic zone adjacent to third degree burns. *Acad Emerg Med* 15, 549-554 (2008).
15. Kallinen, O., et al. Comparison of premortem clinical diagnosis and autopsy findings in patients with burns. *Burns* 34, 595-602 (2008).
16. Barret, J. P. & Herndon, D. N. Effects of burn wound excision on bacterial colonization and invasion. *Plast Reconstr Surg* 111, 744-750; discussion 751-742 (2003).
17. Erol, S., Altoparlak, U., Akcay, M. N., Celebi, F. & Parlak, M. Changes of microbial flora and wound colonization in burned patients. *Burns* 30, 357-361 (2004).
18. Bang, R. L., Sharma, P. N., Sanyal, S. C. & Al Najjadah, I. Septicaemia after burn injury: a comparative study. *Burns* 28, 746-751 (2002).
19. Mason, A. D., Jr., McManus, A. T. & Pruitt, B. A., Jr. Association of burn mortality and bacteremia. A 25-year review. *Arch Surg* 121, 1027-1031 (1986).
20. Tredget, E. E., Rennie, R., Burrell, R. E. & Logsetty, S. Infections in the thermally injured patient, in *Evidence Based Infectious Disease* (ed. Mark Loeb, M. S., and Fiona Smaill) pp. 269-282 (BMJ Books, London, 2004).
21. Horvath, E. E., et al. Fungal wound infection (not colonization) is independently associated with mortality in burn patients. *Ann Surg* 245, 978-985 (2007).
22. Revathi, G., Puri, J. & Jain, B. K. Bacteriology of burns. *Burns* 24, 347-349 (1998).
23. Steer, J. A., Papini, R. P., Wilson, A. P., McGrouther, D. A. & Parkhouse, N. Quantitative microbiology in the management of burn patients. I. Correlation between quantitative and qualitative burn wound biopsy culture and surface alginate swab culture. *Burns* 22, 173-176 (1996).
24. Heimbach, D. M. & Faucher, L. D. Principles of burn surgery, in *Principles and Practice of Burn Surgery* (eds. Herndon, D. N. & Barret-Nerin, J. P.) pp. 135-162 (Marcel Dekker, New York, 2005).
25. Weber, S. M. G., T. A. Wax, M. K. Skin Grafts, Split-Thickness. (eMedicine, 2008).
26. Deitch, E. A. Opsonic activity of blister fluid from burn patients. *Infect Immun* 41, 1184-1189 (1983).
27. Deitch, E. A. & Clothier, J. Burns in the elderly: an early surgical approach. *J Trauma* 23, 891-894 (1983).
28. Deitch, E. A. & Smith, B. J. The effect of blister fluid from thermally injured patients on normal lymphocyte transformation. *J Trauma* 23, 106-110 (1983).
29. Deitch, E. A., Wheelahan, T. M., Rose, M. P., Clothier, J. & Cotter, J. Hypertrophic burn scars: analysis of variables. *J Trauma* 23, 895-898 (1983).
30. Bombaro, K. M., et al. What is the prevalence of hypertrophic scarring following burns?*Burns* 29, 299-302 (2003).
31. Baker, R. H., Townley, W. A., McKeon, S., Linge, C. & Vijh, V. Retrospective study of the association between hypertrophic burn scarring and bacterial colonization. *J Burn Care Res* 28, 152-156 (2007).
32. Martineau, L. & Davis, S. C. Controlling Methicillin Resistant *Staphyloccocus aureus* and *Pseudomonas aeruginosa* Wound Infections with a Novel Biomaterial. *Journal of Investigative Surgery* 20, 217-227 (2007).
33. Barillo, D. J. Topical Antimicrobials in Burn Wound Care: A Recent History. *Wounds* 20, 192-198 (2008).
34. Cioffi, W. G., Rue III, L. W., Buescher, T. M. & Pruitt Jr., B. A. A brief history and the pathophysiology of burns, in *Conventional Warfare: Ballistic, Blast, and Burn Injuries* (ed. Zajtchuk, R.F.B.a.R.) 337-348 (US Army Medical Department, Office of The Surgeon General, - - - ).
35. Bertek Pharmaceuticals, I. SULFAMYLON (Mafenide Acetate, USP) FOR 5% TOPICAL SOLUTION DESCRIPTION. (www.fda.gov/cder/foi/label/1998/19832lbl.pdf).
36. Falcone, P. A., Harrison, H. N., Sowemimo, G. O. & Reading, G. P. Mafenide acetate concentrations and bacteriostasis in experimental burn wounds treated with a three-layered laminated mafenide-saline dressing. *Ann Plast Surg* 5, 266-269 (1980).
37. Murphy, R. C., Kucan, J. O., Robson, M. C. & Heggers, J. P. The effect of 5% mafenide acetate solution on bacterial control in infected rat burns. *J Trauma* 23, 878-881 (1983).
38. Heggers, J. P., et al. Antimicrobial Susceptibility of Mafenide Acetate 5% with Nystatin 10,000 U/ml Solution: Synergy or Antagonism. *J Burns & Surg Wound Caret*, 1-4 (2003).
39. Barret, J. P. Management of superficial burns, in *Principles and Practice of Burn Surgery* (eds. Herndon, D. N. & Barret-Nerin, J. P.) pp. 163-186 (Marcel Dekker, New York, 2005).
40. Gallant-Behm, C. L., et al. Comparison of in vitro disc diffusion and time kill-kinetic assays for the evaluation of antimicrobial wound dressing efficacy. *Wound Repair Regen* 13, 412-421 (2005).
41. Kucan, J. O., Robson, M. C., Heggers, J. P. & Ko, F. Comparison of silver sulfadiazine, povidone-iodine and physiologic saline in the treatment of chronic pressure ulcers. *J Am Geriatr Soc* 29, 232-235 (1981).
42. Ovington, L. G. The truth about silver. *Ostomy Wound Manage* 50, 1S-10S (2004).
43. Leaper, D. J. Silver dressings: their role in wound management. *Int Wound J* 3, 282-294 (2006).
44. Silver, S., Phung le, T. & Silver, G. Silver as biocides in burn and wound dressings and bacterial resistance to silver compounds. *J Ind Microbiol Biotechnol* 33, 627-634 (2006).
45. Seymour, C. Audit of catheter-associated UTI using silver alloy-coated Foley catheters. *Br J Nurs* 15, 598-603 (2006).

46. Hardes, J., et al. Lack of toxicological side-effects in silver-coated megaprostheses in humans. *Biomaterials* 2001 August; 22(15):2095-105. 28, 2869-2875 (2007).
47. Atiyeh, B. S., Costagliola, M., Hayek, S. N. & Dibo, S. A. Effect of silver on burn wound infection control and healing: review of the literature. *Burns* 33, 139-148 (2007).
48. Burd, A., et al. A comparative study of the cytotoxicity of silver-based dressings in monolayer cell, tissue explant, and animal models. *Wound Repair Regen* 15, 94-104 (2007).
49. Demling, R. H. & Leslie DeSanti, M. D. The rate of re-epithelialization across meshed skin grafts is increased with exposure to silver. *Burns* 28, 264-266 (2002).
50. Tian, J., et al. Topical Delivery of Silver Nanoparticles Promotes Wound Healing. *ChemMedChem* 2, 129-136 (2007).
51. Sun, T., Jackson, S., Haycock, J. W. & MacNeil, S. Culture of skin cells in 3D rather than 2D improves their ability to survive exposure to cytotoxic agents. *J Biotechnol* 122, 372-381 (2006).
52. Lok, C. N., et al. Silver nanoparticles: partial oxidation and antibacterial activities. *J Biol Inorg Chem* 12, 527-534 (2007).
53. Morones, J. R., et al. The bactericidal effect of silver nanoparticles. *Nanotechnology* 16, 2346-2353 (2005).
54. Lyczak, J. B. & J., S. P. Nanocrystalline silver inhibits antibiotic-, antiseptic-resistant bacteria, in *American Society for Clinical Pharmacology and Therapeutics* (February 2005).
55. Walker, M., Cochrane, C. A., Bowler, P. G., Parsons, D. & Bradshaw, P. Silver deposition and tissue staining associated with wound dressings containing silver. *Ostomy Wound Manage* 52, 42-44, 46-50 (2006).
56. Kucan, J. O. & Heggers, J. P. The potential benefit of 5% Sulfamylon Solution in the treatment of *Acinetobacter baumannii*-contaminated traumatic war wounds. *J Burns Wounds* 4, e3 (2005).
57. Harrison, H. N., Blackmore, W. P., Bales, H. W. & Reeder, W. The absorption of C 14-labeled Sulfamylon acetate through burned skin. I. Experimental methods and initial observations. *J Trauma* 12, 986-993 (1972).
58. Barret, J. P., Wolf, S. E., Desai, M. H. & Herndon, D. N. Cost-efficacy of cultured epidermal autografts in massive pediatric burns. *Ann Surg* 231, 869-876 (2000).
59. Falanga, V. & Iwamoto, S. Chapter 249. Wound Repair: Mechanisms and Practical Considerations, in *Fitzpatrick's Dermatology in General Medicine*, 7th Edition (ed. Wolff K, G. L., Katz S I, Gilchrest B, Paller A S, Leffell D J) (http://www.accessmedicine.com/content.aspx?alD=3006805.).
60. Capla, J. M., et al. Skin graft vascularization involves precisely regulated regression and replacement of endothelial cells through both angiogenesis and vasculogenesis. *Plast Reconstr Surg* 117, 836-844 (2006).
61. Lee, L. F., Porch, J. V., Spenler, W. & Garner, W. L. Integra in lower extremity reconstruction after burn injury. *Plast Reconstr Surg* 121, 1256-1262 (2008).
62. LifeSciences, I. Integra Dermal Regeneration Template Package Insert RMS#51000-1204-6. (2003).
63. Helgeson, M. D., Potter, B. K., Evans, K. N. & Shawen, S. B. Bioartificial dermal substitute: a preliminary report on its use for the management of complex combat-related soft tissue wounds. *J Orthop Trauma* 21, 394-399 (2007).
64. Jeschke, M. G., et al. Development of new reconstructive techniques: use of Integra in combination with fibrin glue and negative-pressure therapy for reconstruction of acute and chronic wounds. *Plast Reconstr Surg* 113, 525-530 (2004).
65. Molnar, J. A., et al. Acceleration of Integra incorporation in complex tissue defects with subatmospheric pressure. *Plast Reconstr Surg* 113, 1339-1346 (2004).
66. Druecke, D., et al. Modulation of scar tissue formation using different dermal regeneration templates in the treatment of experimental full-thickness wounds. *Wound Repair Regen* 12, 518-527 (2004).
67. Wieman, T. J., Smiell, J. M. & Su, Y. Efficacy and safety of a topical gel formulation of recombinant human platelet-derived growth factor-BB (becaplermin) in patients with chronic neuropathic diabetic ulcers. A phase III randomized placebo-controlled double-blind study. *Diabetes Care* 21, 822-827 (1998).
68. Wieman, T. J. Clinical efficacy of becaplermin (rhPDGF-BB) gel. Becaplermin Gel Studies Group. *Am J Surg* 176, 74S-79S (1998).
69. Ridgway, H. K., Mellonig, J. T. & Cochran, D. L. Human histologic and clinical evaluation of recombinant human platelet-derived growth factor and beta-tricalcium phosphate for the treatment of periodontal intraosseous defects. *Int J Periodontics Restorative Dent* 28, 171-179 (2008).
70. FDA. SUMMARY OF SAFETY AND EFFECTIVENESS DATA: GEM 21STM (Growth Factor Enhanced Matrix).
71. Danilenko, D. M., et al. Growth factors in porcine full and partial thickness burn repair. Differing targets and effects of keratinocyte growth factor, platelet-derived growth factor-BB, epidermal growth factor, and neu differentiation factor. *Am J Pathol* 147, 1261-1277 (1995).
72. Smiell, J. M., et al. Efficacy and safety of becaplermin (recombinant human platelet-derived growth factor-BB) in patients with nonhealing, lower extremity diabetic ulcers: a combined analysis of four randomized studies. *Wound Repair Regen* 7, 335-346 (1999).
73. Hollister, C. & Li, V. W. Using angiogenesis in chronic wound care with becaplermin and oxidized regenerated cellulose/collagen. *Nurs Clin North Am* 42, 457-465, vii (2007).
74. Jin, Q., et al. Nanofibrous scaffolds incorporating PDGF-BB microspheres induce chemokine expression and tissue neogenesis in vivo. *PLoS ONE* 3, e1729 (2008).
75. Galkowska, H., Wojewodzka, U. & Olszewski, W. L. Chemokines, cytokines, and growth factors in keratinocytes and dermal endothelial cells in the margin of chronic diabetic foot ulcers. *Wound Repair Regen* 14, 558-565 (2006).
76. Ansel, J. C., et al. Human keratinocytes are a major source of cutaneous platelet-derived growth factor. *J Clin Invest* 92, 671-678 (1993).
77. Chan, R. K., et al. Effect of recombinant platelet-derived growth factor (Regranex) on wound closure in genetically diabetic mice. *J Burn Care Res* 27, 202-205 (2006).
78. Hijjawi, J., et al. Platelet-derived growth factor B, but not fibroblast growth factor 2, plasmid DNA improves survival of ischemic myocutaneous flaps. *Arch Surg* 139, 142-147 (2004).
79. Brown, M. B., Traynor, M. J., Martin, G. P. & Akomeah, F. K. Transdermal drug delivery systems: skin perturbation devices. *Methods Mol Biol* 437, 119-139 (2008).
80. Manafi, A., Hashemlou, A., Momeni, P. & Moghimi, H. R. Enhancing drugs absorption through third-degree burn wound eschar. *Burns* 34, 698-702 (2008).

81. Stefanides, M. M., Sr., Copeland, C. E., Kominos, S. D. & Yee, R. B. In vitro penetration of topical antiseptics through eschar of burn patients. *Ann Surg* 183, 358-364 (1976).
82. Percival, S. L., Bowler, P. & Woods, E. J. Assessing the effect of an antimicrobial wound dressing on biofilms. *Wound Repair Regen* 16, 52-57 (2008).
83. Percival, S. L., Bowler, P. G. & Dolman, J. Antimicrobial activity of silver-containing dressings on wound microorganisms using an in vitro biofilm model. *Int Wound J* 4, 186-191 (2007).
84. Thomas, B. J. & Finnin, B. C. The transdermal revolution. *Drug Discov Today* 9, 697-703 (2004).
85. Sinha, R., Sharma, N. & Agarwal, R. K. Subeschar clysis in deep burns. *Burns* 29, 854-856 (2003).
86. Lee, J. W., Park, J. H. & Prausnitz, M. R. Dissolving microneedles for transdermal drug delivery. *Biomaterials* 29, 2113-2124 (2008).
87. Murray, C. K., et al. Prevention and management of infections associated with combat-related extremity injuries. *J Trauma* 64, S239-251 (2008).
88. Banga, A. K. New technologies to allow transdermal delivery of therapeutic proteins and small water-soluble drugs. *Am J Drug Deliv* 4, 221-230 (2006).
89. Coulman, S., Allender, C. & Birchall, J. Microneedles and other physical methods for overcoming the stratum corneum barrier for cutaneous gene therapy. *Crit Rev Ther Drug Carrier Syst* 23, 205-258 (2006).
90. Coulman, S. A., et al. Minimally invasive cutaneous delivery of macromolecules and plasmid DNA via microneedles. *Curr Drug Deliv* 3, 65-75 (2006).
91. Sullivan, T. P., Eaglstein, W. H., Davis, S. C. & Mertz, P. The pig as a model for human wound healing. *Wound Repair Regen* 9, 66-76 (2001).
92. Singer, A. J. & McClain, S. A. A porcine burn model, in *Wound Healing: Methods and Protocols* (eds. DiPietro, L. A. & Burns, A. J.) pp. 107-119 (Humana Press, New York, 2003).
93. Papp, A., et al. The progression of burn depth in experimental burns: a histological and methodological study. *Burns* 30, 684-690 (2004).
94. Rose, E. H., Vistnes, L. M. & Ksander, G. A. The panniculus carnosus in the domestic pig. *Plast Reconstr Surg* 59, 94-97 (1977).
95. Montandon, D., D'Andiran, G. & Gabbiani, G. The mechanism of wound contraction and epithelialization: clinical and experimental studies.—*Clin Plast Surg* 1977 July; 4(3):325-46. 4, 325-346 (1977).
96. Renkielska, A., Nowakowski, A., Kaczmarek, M. & Ruminski, J. Burn depths evaluation based on active dynamic IR thermal imaging—a preliminary study. *Burns* 32, 867-875 (2006).
97. Middelkoop, E., et al. Porcine wound models for skin substitution and burn treatment. *Biomaterials* 25, 1559-1567 (2004).
98. Upton, Z., et al. Vitronectin: growth factor complexes hold potential as a wound therapy approach. *J Invest Dermatol* 128, 1535-1544 (2008).
99. Branski, L. K., et al. A porcine model of full-thickness burn, excision and skin autografting. *Burns* (2008).
100. Cuttle, L., et al. A porcine deep dermal partial thickness burn model with hypertrophic scarring. *Burns* 32, 806-820 (2006).
101. Bechert, T., Steinrucke, P. & Guggenbichler, J. P. A new method for screening anti-infective biomaterials. *Nat Med* 6, 1053-1056 (2000).
102. Vardaxis, N. J., Brans, T. A., Boon, M. E., Kreis, R. W. & Marres, L. M. Confocal laser scanning microscopy of porcine skin: implications for human wound healing studies. *J Anat* 190 (Pt 4), 601-611 (1997).
103. Rezvani, M., Hamlet, R., Hopewell, J. W. & Sieber, V. K. Time and dose-related changes in the thickness of pig skin after irradiation with single doses of $90Sr/^{90}Y$ beta-rays. *Int J Radiat Biol* 65, 497-502 (1994).
104. Muhammad N A, B. W., Harris M R, Weiss J. Evaluation of hydroxypropyl methylcellulose phthalate 50 as film forming polymer from aqueous dispersion systems. *Drug Dev Ind Pharm* 18, 1787-1797 (1992).
105. Clements, J. M., et al. Two PDGF-B chain residues, arginine 27 and isoleucine 30, mediate receptor binding and activation. *Embo J* 10, 4113-4120 (1991).
106. Goa, K. L. & Benfield, P. Hyaluronic acid. A review of its pharmacology and use as a surgical aid in ophthalmology, and its therapeutic potential in joint disease and wound healing. *Drugs* 47, 536-566 (1994).
107. Luo, Y., Kirker, K. R. & Prestwich, G. D. Cross-linked hyaluronic acid hydrogel films: new biomaterials for drug delivery. *J Control Release* 69, 169-184 (2000).
108. Alt, V., et al. In vitro testing of antimicrobial activity of bone cement. *Antimicrob Agents Chemother* 48, 4084-4088 (2004).
109. Kreiswirth, B. N., et al. The toxic shock syndrome exotoxin structural gene is not detectably transmitted by a prophage. *Nature* 305, 709-712 (1983).
110. Cheung, A. L. & Projan, S. J. Cloning and sequencing of sarA of *Staphylococcus aureus*, a gene required for the expression of agr. *J Bacteriol* 176, 4168-4172 (1994).
111. Compagnone-Post, P., Malyankar, U. & Khan, S. A. Role of host factors in the regulation of the enterotoxin B gene. *J Bacteriol* 173, 1827-1830 (1991).
112. Zhang, X. J., et al. Topical Sulfamylon cream inhibits DNA and protein synthesis in the skin donor site wound. *Surgery* 139, 633-639 (2006).
113. Pierce, G. F., et al. In vivo incisional wound healing augmented by platelet-derived growth factor and recombinant c-sis gene homodimeric proteins. *J Exp Med* 167, 974-987 (1988).
114. Lee, M., Chen, T. T., Iruela-Arispe, M. L., Wu, B. M. & Dunn, J. C. Modulation of protein delivery from modular polymer scaffolds. *Biomaterials* 28, 1862-1870 (2007).
115. Alt, V., et al. An in vitro assessment of the antibacterial properties and cytotoxicity of nanoparticulate silver bone cement.—*Biomaterials* 2001 August; 22(15):2095-105. 25, 4383-4391 (2004).
116. Verne, E., et al. Surface characterization of silver-doped bioactive glass.—*Biomaterials* 2001 August; 22(15):2095-105. 26, 5111-5119 (2005).
117. Fu, J., Ji, J., Fan, D. & Shen, J. Construction of antibacterial multilayer films containing nanosilver via layer-by-layer assembly of heparin and chitosan-silver ions complex. *J Biomed Mater Res A* 79, 665-674 (2006).
118. Chen, W., et al. In vitro anti-bacterial and biological properties of magnetron co-sputtered silver-containing hydroxyapatite coating.—*Biomaterials* 2001 August; 22(15):2095-105. 27, 5512-5517 (2006).
119. McCauley, R. L., et al. In vitro toxicity of topical antimicrobial agents to human fibroblasts. *J Surg Res* 46, 267-274 (1989).
120. Cooper, M. L., Boyce, S. T., Hansbrough, J. F., Foreman, T. J. & Frank, D. H. Cytotoxicity to cultured human keratinocytes of topical antimicrobial agents. *J Surg Res* 48, 190-195 (1990).

121. McCauley, R. L., et al. Differential inhibition of human basal keratinocyte growth to silver sulfadiazine and mafenide acetate. *J Surg Res* 52, 276-285 (1992).
122. Zapata-Sirvent, R. L. & Hansbrough, J. F. Cytotoxicity to human leukocytes by topical antimicrobial agents used for burn care. *J Burn Care Rehabil* 14, 132-140 (1993).
123. Mayes, A. E. & Holyoak, C. D. Repeat mild heat shock increases dermal fibroblast activity and collagen production. *Rejuvenation Res* 11, 461-465 (2008).
124. Boukamp, P., et al. Normal keratinization in a spontaneously immortalized aneuploid human keratinocyte cell line. *J Cell Biol* 106, 761-771 (1988).
125. Nylund, R. & Leszczynski, D. Proteomics analysis of human endothelial cell line EA.hy926 after exposure to GSM 900 radiation. *Proteomics* 4, 1359-1365 (2004).
126. Ferrara, N. Vascular endothelial growth factor: molecular and biological aspects. *Curr Top Microbiol Immunol* 237, 1-30 (1999).
127. Zhang, X., et al. Overexpression of Nell-1, a craniosynostosis-associated gene, induces apoptosis in osteoblasts during craniofacial development. *J Bone Miner Res* 18, 2126-2134 (2003).
128. Soo, C., et al. Ontogenetic transition in fetal wound transforming growth factor-beta regulation correlates with collagen organization. *Am J Pathol* 163, 2459-2476 (2003).
129. Zhang, X., et al. Craniosynostosis in transgenic mice overexpressing Nell-1. *J Clin Invest* 110, 861-870. (2002).
130. Garrett, W. M. & Guthrie, H. D. Detection of Bromodeoxyuridine in Paraffin-embedded Tissue Sections Using Microwave Antigen Retrieval is Dependent on the Mode of Tissue Fixation. *Biochemica* 1, 17-20 (1998).
131. Breuing, K., Kaplan, S., Liu, P., Onderdonk, A. B. & Eriksson, E. Wound fluid bacterial levels exceed tissue bacterial counts in controlled porcine partial-thickness burn infections. *Plait Reconstr Surg* 111, 781-788 (2003).
132. Breuing, K., et al. Growth factors in the repair of partial thickness porcine skin wounds. *Plast Reconstr Surg* 100, 657-664 (1997).
133. Harrison, H. N., Bales, H. W. & Jacoby, F. The absorption into burned skin of Sulfamylon acetate from 5 percent aqueous solution. *J Trauma* 12, 994-998 (1972).

While particular embodiments of the present invention have been shown and described, it can be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A transcutaneous multimodal delivery device (TMDS), comprising a transcutaneous drug delivery (TDD) component and a sustained delivery and retention (SDR) component;
    wherein the TMDS provides a controlled delivery of at least one active agent comprising a first therapeutic drug or a second therapeutic drug where the first therapeutic drug and the second therapeutic drug are the same or different;
    wherein the TDD component comprises dissolvable microneedles at least one of which having a sharp tip and a blunt tip, wherein the sharp tip has a dimension so as to allow the microneedles to penetrate eschar of skin without reaching viable tissue, and wherein the blunt tip is enclosed within the sharp tip and has a tip angle that is less sharp than that of the sharp tip,
    wherein the SDR component comprises a plurality of release control vehicles comprising the first therapeutic drug or second therapeutic drug to provide controlled release of the first therapeutic drug or the second therapeutic drug, and
    wherein the plurality of release control vehicles of the SDR component is enclosed within the blunt tip and the sharp tip of the dissolvable microneedles of the TDD component and released upon dissolution of the dissolvable microneedles.

2. The TMDS of claim 1, wherein the sharp tip and the blunt tip enclosed within completely dissolve within a period ranging from about 10 seconds to about 10 days upon application to a patient.

3. The TMDS of claim 2, wherein the period is selected from the group consisting of 30 seconds, 30 minutes, 1 hr, 2 hr, 5 hr, 10 hr, 24 hr, 2 days, 5 days, and 10 days; and
    wherein the plurality of release control vehicles provides a sustained release of the first therapeutic drug or the second therapeutic drug over a period up to 30 days.

4. The TMDS of claim 1, wherein at least one of the first therapeutic drug and the second therapeutic drug is an antimicrobial agent.

5. The TMDS of claim 4, wherein the antimicrobial agent is selected from group consisting of silver nitrate, nanoparticulate silver ($Ag^{nano}$), mafenide acetate (MA), iodine, and silver sulfadiazine (SDD); wherein the biologically active agent is platelet derived growth factor (PDGF) or isolated human cells encapsulated within the release control vehicle; wherein the isolated human cells comprises a stem cell, a non-stem cell or combination thereof.

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: 5' primer based on sarA sequence

<400> SEQUENCE: 1
tagggagagg ttttaaac                                                 18

6. The TMDS of claim 1, wherein at least one of the first therapeutic drug and the second therapeutic drug is a biologically active agent.

7. The TMDS of claim 1, wherein the dissolvable microneedles are formed from a material comprising a dissolvable polymer.

8. The TMDS of claim 1, wherein the dissolvable microneedles comprise carboxylmethyl cellulose (CMC), a derivative of CMC, hydroxypropyl methylcellulose phthalate (HPMCP), a derivative of HPMCP, or a combination thereof.

9. The TMDS of claim 1, wherein the plurality of release control vehicles comprises a biodegradable polymer.

10. The TMDS of claim 1, wherein the plurality of release control vehicles comprises hyaluronic acid (HA), a derivative of HA, collagen, or a derivative of collagen, or a combination thereof.

11. The TMDS of claim 1, wherein the sharp tip is capable of complete dissolution within about 1 hr upon application to a patient.

12. The TMDS of claim 1, wherein the plurality of release control vehicles is selected from the group consisting of liposomes, nanoparticles, microparticles, dendrimers, soluble polymer conjugates, and a combination thereof, wherein each of the plurality of release control vehicles comprises a targeting ligand Y for targeted delivery of the first therapeutic drug or the second therapeutic drug; and
  wherein the targeting ligand Y is attached to any of the following:
  surface of liposomes of phospholipid bilayer where the first therapeutic drug or the second therapeutic drug is associated within the bilayer and a hydrophilic layer is located inside the bilayer as the hydrophilic core;
  surface of nanoparticles comprising the first therapeutic drug or the second therapeutic drug;
  surface of microparticles the first therapeutic drug or the second therapeutic drug; surface of micelles having a hydrophilic outer shell and a hydrophobic core where the first therapeutic drug or the second therapeutic drug is located in the hydrophobic core;
  surface of dendrimers comprising the first therapeutic drug or the second therapeutic drug; and soluble polymer conjugates where the first therapeutic drug or the second therapeutic drug is attached to side chains of polymer.

13. A method of treating or ameliorating a skin condition or non-skin condition, comprising applying to a patient having the skin condition a transcutaneous multimodal delivery device (TMDS) comprising a transcutaneous drug delivery (TDD) component and a sustained delivery and retention (SDR) component,
  wherein the skin condition is wounded skin or diseased skin and the non-skin condition is muscle injury, bone injury, or cartilage injury;
  wherein the TMDS provides a controlled delivery of at least one active agent comprising a first therapeutic drug or a second therapeutic drug where the first therapeutic drug and the second therapeutic drug is the same or different;
  wherein the TDD component comprises dissolvable microneedles having a dimension so as to allow the microneedles to penetrate eschar of skin without reaching viable tissue,
  wherein the TDD component comprises dissolvable microneedles at least one of which having a sharp tip and a blunt tip, wherein the sharp tip has a dimension so as to allow the microneedles to penetrate eschar of skin without reaching viable tissue, and wherein the blunt tip is enclosed within the sharp tip and has a tip angle that less sharp than that of the sharp tip,
  wherein the SDR component comprises a plurality of release control vehicles comprising the first therapeutic drug or second therapeutic drug to provide controlled release of the first therapeutic drug or the second therapeutic drug, and
  wherein the plurality of release control vehicles of the SDR component is enclosed within the blunt tip and the sharp tip of the dissolvable microneedles of the TDD component and released upon dissolution of the dissolvable microneedles.

14. The method of claim 13, wherein the dissolvable microneedles completely dissolve within a period ranging from about 10 seconds to about 10 days upon application to a patient.

15. The method of claim 14, wherein the period is selected from the group consisting of 30 seconds, 30 minutes, 1 hr, 2 hr, 5 hr, 10 hr, 24 hr, 2 days, 5 days, and 10 days; and
  wherein the plurality of release control vehicles provides a sustained release of the first therapeutic drug or the second therapeutic drug over a period up to 30 days.

16. The method of claim 13, wherein at least one of the first therapeutic drug and the second therapeutic drug is an antimicrobial agent.

17. The method of claim 16, wherein the antimicrobial agent is selected from group consisting of silver nitrate, nanoparticulate silver ($Ag^{nano}$), mafenide acetate (MA), iodine, and silver sulfadiazine (SDD); and wherein the biologically active agent is platelet derived growth factor (PDGF).

18. The method of claim 13, wherein at least one of the first therapeutic drug and the second therapeutic drug is a biologically active agent.

19. The method of claim 13, wherein the dissolvable microneedles are formed from a material comprising a dissolvable polymer.

20. The method of claim 13, wherein the dissolvable microneedles comprise carboxylmethyl cellulose (CMC), a derivative of CMC, hydroxypropyl methylcellulose phthalate (HPMCP), a derivative of HPMCP, or a combination thereof.

21. The method of claim 13, wherein the plurality of release control vehicles comprises a biodegradable polymer.

22. The method of claim 13, wherein the plurality of release control vehicles comprises hyaluronic acid (HA), a derivative of HA, collagen, or a derivative of collagen, or a combination thereof.

23. The method of claim 13, wherein the skin condition is burn wound or one of other non-healing or infected cutaneous wounds.

24. The method of claim 13, wherein the skin condition is a chronic diabetic ulcer or necrotizing fasciitis.

25. The method of claim 13, wherein the sharp tip is capable of complete dissolution within about 1 hr upon application to a patient.

26. The method of claim 13, wherein the plurality of release control vehicles is selected from the group consisting of liposomes, nanoparticles, microparticles, dendrimers, soluble polymer conjugates, and a combination thereof, wherein each of the plurality of release control vehicles comprises a targeting ligand Y for targeted delivery of the first therapeutic drug or the second therapeutic drug; and
  wherein the targeting ligand Y is attached to any of the following:
  surface of liposomes of phospholipid bilayer where the first therapeutic drug or the second therapeutic drug is associated within the bilayer and a hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

27. A method of fabricating a transcutaneous multimodal delivery device (TMDS), comprising:

forming a transcutaneous drug delivery (TDD) component;

forming a sustained delivery and retention (SDR) component; and forming the TMDS, wherein the TMDS provides a controlled delivery of at least one active agent comprising a first therapeutic drug or a second therapeutic drug where the first therapeutic drug and the second therapeutic drug is the same or different;

wherein the TDD component comprises dissolvable microneedles at least one of which having a sharp tip and a blunt tip, wherein the sharp tip has a dimension so as to allow the microneedles to penetrate eschar of skin without reaching viable tissue, and wherein the blunt tip is enclosed within the sharp tip and has a tip angle that is less sharp than that of the sharp tip, wherein the SDR component comprises a plurality of release control vehicles comprising the first therapeutic drug or second therapeutic drug to provide controlled release of the first therapeutic drug or the second therapeutic drug, and wherein the plurality of release control vehicles of the SDR component is enclosed within the blunt tip and the sharp tip of the dissolvable microneedles of the TDD component and released upon dissolution of the dissolvable microneedles.

28. The method of claim 27, wherein the dissolvable microneedles completely dissolve within a period ranging from about 10 seconds to about 10 days upon application to a patient.

29. The method of claim 28, wherein the period is selected from the group consisting of 30 seconds, 30 minutes, 1 hr, 2 hr, 5 hr, 10 hr, 24 hr, 2 days, 5 days, and 10 days; and wherein the plurality of release control vehicles provides a sustained release of the first therapeutic drug or the second therapeutic drug over a period from above 10 days to up to 30 days.

30. The method of claim 27, wherein at least one of the first therapeutic drug and the second therapeutic drug is an antimicrobial agent.

31. The method of claim 30, wherein the antimicrobial agent is selected from group consisting of silver nitrate, nanoparticulate silver ($Ag^{nano}$), mafenide acetate (MA), iodine, and silver sulfadiazine (SDD); and wherein the biologically active agent is platelet derived growth factor (PDGF).

32. The method of claim 27, wherein at least one of the first therapeutic drug and the second therapeutic drug is a biologically active agent.

33. The method of claim 27, wherein the dissolvable microneedles are formed from a material comprising a dissolvable polymer.

34. The method of claim 27, wherein the dissolvable microneedles comprise carboxylmethyl cellulose (CMC), a derivative of CMC, hydroxypropyl methylcellulose phthalate (HPMCP), a derivative of HPMCP, or a combination thereof.

35. The method of claim 27, wherein the plurality of release control vehicles comprises a biodegradable polymer.

36. The method of claim 27, wherein the plurality of release control vehicles comprises hyaluronic acid (HA), a derivative of HA, collagen, or a derivative of collagen, or a combination thereof.

37. The method of claim 27, wherein the sharp tip is capable of complete dissolution within about 1 hr upon application to a patient.

38. The method of claim 27, wherein the plurality of release control vehicles is selected from the group consisting of liposomes, nanoparticles, microparticles, dendrimers, soluble polymer conjugates, and a combination thereof, wherein each of the plurality of release control vehicles comprises a targeting ligand Y for targeted delivery of the first therapeutic drug or the second therapeutic drug; and wherein the targeting ligand Y is attached to any of the following:

surface of liposomes of phospholipid bilayer where the first therapeutic drug or the second therapeutic drug is associated within the bilayer and a hydrophilic layer is located inside the bilayer as the hydrophilic core;

surface of nanoparticles comprising the first therapeutic drug or the second therapeutic drug;

surface of microparticles the first therapeutic drug or the second therapeutic drug;

surface of micelles having a hydrophilic outer shell and a hydrophobic core where the first therapeutic drug or the second therapeutic drug is located in the hydrophobic core;

surface of dendrimers comprising the first therapeutic drug or the second therapeutic drug; and soluble polymer conjugates where the first therapeutic drug or the second therapeutic drug is attached to side chains of polymer.

39. A transcutaneous multimodal delivery device (TMDS), comprising a transcutaneous drug delivery (TDD) component and a sustained delivery and retention (SDR) component;

wherein the TMDS provides a controlled delivery of at least one active agent comprising a first therapeutic drug or a second therapeutic drug where the first therapeutic drug and the second therapeutic drug are the same or different;

wherein the TDD component comprises dissolvable microneedles at least one of which having a sharp tip and a blunt tip, wherein the sharp tip has a dimension so as to allow the microneedles to penetrate eschar of skin without reaching viable tissue, and wherein the blunt tip is enclosed within the sharp tip and has a tip angle that is less sharp than that of the sharp tip, wherein the SDR component comprises a plurality of release control vehicles comprising the first therapeutic drug or second therapeutic drug to provide controlled release of the first therapeutic drug or the second therapeutic drug, and wherein the blunt tip and the sharp tip of the dissolvable microneedles are formed from a material comprising a dissolvable polymer, and wherein the plurality of release control vehicles of the SDR component is enclosed within the blunt tip and the sharp tip of the dissolvable microneedles of the TDD component and released upon dissolution of the dissolvable microneedles.

\* \* \* \* \*